(12) United States Patent
Hua et al.

(10) Patent No.: US 7,687,064 B2
(45) Date of Patent: Mar. 30, 2010

(54) **METHODS AND COMPOSITIONS ASSOCIATED WITH ADMINISTRATION OF AN EXTRACT OF *GANODERMA LUCIDUM***

(75) Inventors: Kuo-Feng Hua, Taipei (TW); Hsien-Yeh Hsu, Taipei (TW); Chi-Huey Wong, Rancho Santa Fe, CA (US)

(73) Assignee: Academia Sinica, Taipei (TW)

( * ) Notice: Subject to any disclaimer, the term of this patent is extended or adjusted under 35 U.S.C. 154(b) by 34 days.

(21) Appl. No.: 11/534,204

(22) Filed: Sep. 21, 2006

(65) Prior Publication Data

US 2007/0105814 A1     May 10, 2007

Related U.S. Application Data

(63) Continuation-in-part of application No. PCT/US2005/036961, filed on Oct. 14, 2005, which is a continuation-in-part of application No. 10/213,257, filed on Aug. 6, 2002, now Pat. No. 7,135,183.

(60) Provisional application No. 60/310,285, filed on Aug. 6, 2001, provisional application No. 60/619,263, filed on Oct. 14, 2004.

(51) Int. Cl.
| | |
|---|---|
| A61K 36/06 | (2006.01) |
| A61K 9/00 | (2006.01) |
| A61K 47/00 | (2006.01) |
| A23K 1/17 | (2006.01) |

(52) U.S. Cl. .................. 424/195.15; 424/400; 424/439; 424/442

(58) Field of Classification Search ....................... None
See application file for complete search history.

(56) References Cited

U.S. PATENT DOCUMENTS

| | | | |
|---|---|---|---|
| 4,522,811 A | 6/1985 | Eppstein et al. | |
| 5,334,704 A | 8/1994 | Tsunoo et al. | |
| 6,395,310 B1 | 5/2002 | Iwasaki | |
| 6,464,982 B1 | 10/2002 | Lam | |
| 6,471,860 B1 | 10/2002 | Miltenyi et al. | |
| 6,613,754 B1 | 9/2003 | Wu | |
| 7,135,183 B1 | 11/2006 | Wang et al. | |
| 7,323,176 B2 | 1/2008 | Wang et al. | |
| 2003/0068329 A1 | 4/2003 | Kosuna et al. | |
| 2003/0095981 A1 | 5/2003 | Wong et al. | |
| 2007/0104729 A1 | 5/2007 | Wang et al. | |
| 2007/0105814 A1 | 5/2007 | Hua et al. | |
| 2007/0231339 A1 | 10/2007 | Yu et al. | |
| 2008/0214442 A1 | 9/2008 | Yu et al. | |
| 2008/0247989 A1 | 10/2008 | Shih et al. | |

FOREIGN PATENT DOCUMENTS

| | | |
|---|---|---|
| WO | WO/2006/044616 | 4/2006 |
| WO | WO/2007/047021 | 4/2007 |
| WO | WO/2008/036421 | 3/2008 |

OTHER PUBLICATIONS

Mizuno ( Fractination Chemical Modification and Antitumor activity of Wqater-insoluble Plysaccharides or the Fruiting-Body of *Gandoerma-lucidum*, Nippon Nogikagaku Kaishi, (1985), vol. 59, No. 11, pp. 1143-1152, please see Abstract).*
Mizuno et al. (Fractionation chemical modification and antitumor activity of water-insoluble polysaccharides of the fruiting-body of *Ganoderma-lucidum*, Nippon Nogeidagaku Kaishi, (1985) vol. 59, No. 11, pp. 1143-1152).*
Blomberg K. et al., *Fluorescent europium chelates as target cell markers in the assessment of natural killer cell cytotoxicity*, J. Immunol. Methods, 1993, vol. 160, pp. 27-34.
Bowden, R. et al., *Alteration of Cytokine Levels in Murine Retrovirus Infection: Modulation by Combination Therapy*, International Journal of Immunopharmacology 1999, vol. 21, pp. 815-827.
Braciale T. et al., *Antigen presentation: structural themes and functional variations*, Immunology Today, 1991, vol. 12, No. 4, pp. 124-129.
Bronte V. et al., *IL-2 Enhances the Function of Recombinant Poxvirus-Based Vaccines in the Treatment of Established Pulmonary Metastases*, J. Immunol., 1995, vol. 154, pp. 5282-5292.
Chen H. et al., *Studies on the immuno-modulating and anti-tumor activities of Ganoderma lucidum (Reishi) polysaccharides*, Bioorg. Med. Chem., 2004, vol. 12, pp. 5595-5601.
Chen-Bettecken U. et al., *IgM RNA switch from membrane to secretory form is prevented by adding antireceptor antibody to bacterial lipopolysaccharide-stimulated murine primary B-cell cultures*, Proc. Natl. Acad. Sci., USA, 1985, vol. 82, pp. 7384-7388.
Chien C., *Polysaccharides of Ganoderma lucidum alter cell immunophenotypic expression and enhance $CD56^+$ NK-cell cytotoxicity in cord blood*, Bioorg. Med. Chem., 2004, vol. 12, pp. 5603-5609.
Feltkamp M. et al., *Cytotoxic T lymphocytes raised against a subdominant epitope offered as a synthetic peptide eradicate human papillomavirus type 16-induced tumors*, Eur. J. Immunol., 1995, vol. 25, pp. 2638-2642.

(Continued)

*Primary Examiner*—Christopher R Tate
*Assistant Examiner*—Randall Winston
(74) *Attorney, Agent, or Firm*—Luce Forward Hamilton & Scripps, LLP; Mark Krietzman

(57) ABSTRACT

The present disclosure provides methods for increasing the lipopolysaccharide-induced secretion of IL-1 by macrophages, for increasing serum levels of IL-1 in a mammal, for increasing the serum level of IL-1 receptor antagonist (IL-1Ra) in a mammal, for increasing the secretion of IL-1 by a monocyte, for increasing the secretion of IL-1Ra by a monocyte, for increasing the secretion of IL-1Ra by a macrophage, for increasing expression of TLR4 on the surface of a macrophage, for increasing expression of CD14 on the surface of macrophage, for increasing the uptake and clearance of lipopolysaccharide (LPS) by a LPS-stimulated macrophage, and for increasing lipopolysaccharide (LPS)-stimulated activation of at least one of ERK, JNK, and p38 in a macrophage. The methods of the disclosure involve the administration to mammals and immune cells of a fucose-containing glycoprotein fraction from *Ganoderma lucidum*.

6 Claims, 19 Drawing Sheets

OTHER PUBLICATIONS

Franz, G., *Polysaccharides in Pharmacy: Current Applications and Future Concepts*, Planta Medica, 1989, vol. 55, pp. 493-497.

Furusawa, E. et al., *Antitumor Activity of Ganoderma lucidum, an Edible Mushroom, on Intraperitoneally Implanted Lewis Lung Carcinoma in Synergenic Mice*, Phytotherapy Research, vol. 6, 1992, pp. 300-304.

Grohmann U. et al, $CD8^+$ *cell activation to a major mastocytoma rejection antigen, P815AB: requirement for tumor helper peptides in priming for skin test reactivity to a P815AB-related peptide*, Eur. J. Immunol., 1995, vol. 25, pp. 2797-2802.

Halhoul M. et al., *Differential Determination of Glucose and Fructose, and Glucose- and Fructose-Yielding Substances with Anthrone*, Anal. Biochem., 1972, vol. 50, pp. 337-343.

Hellman M. et al., *Separation of Isomeric Polyphenyls by Adsorption Chromatography*, 1990, Analytical Chemistry, pp. 1206-1210.

Henderson R. et al., *Human Tumor Antigens are Ready to Fly*, Advances in Immunology, 1996, vol. 62, pp. 217-256.

Hsu H. et al., *Extract of Reishi Polysaccharides Induces Cytokine Expression via TLR4-Modulated Protein Kinase Signaling Pathways*, J. Immunol., 2004, vol. 173, pp. 5989-5999.

Jermyn M., *Increasing the Sensitivity of the Anthrone Method for Carbohydrate*, Anal. Biochem., 1975, vol. 68, pp. 332-335.

Kim B. et al., *Antineoplastic Components of Korean Basidomycetes*, Korean Journal of Mycology, 1980, vol. 8, No. 2, pp. 107-114.

Kovacsovics-Bankowski M. et al., *A Phagosome-to-Cytosol Pathway for Exogenous Antigens Presented on MHC Class I Molecules*, Science, 1995, vol. 267, pp. 243-246.

Lin K. et al., *Reishi Polysaccharides Induce Immunoglobulin Production through the TLR4/TLR2-mediated Induction of Transcription Factor Blimp-I*, J. Biol. Chem., 2006, vol. 281, No. 34, pp. 24111-24123.

Lo C. et al., *Simple fractionation of phospholipase $A_2$ analogues from snake venom by high-performance liquid chromatography*, J. Chromatogr. 1990, vol. 530, pp. 129-136.

Miyazaki, T. et al., *Structural Examination of an Alkali-Extracted, Water-Soluble Heteroglycan of the Fungus Ganoderma lucidum*, Carbohydrate Research, 1982, vol. 109, pp. 290-294.

Mizuno et al., Fractionation, *Chemical Modification and Antitumor Activity of Water-insoluble Polysaccharides of the Fruiting Body of Ganoderma lucidum*, Journal of the Agricultural Chemical Society of Japan (Nippon Nôgeikagaku Kaishi), 1985, vol. 59, No. 11, pp. 1143-1151. [English language abstract enclosed].

Mosmann, T., *Rapid Colorimetric Assay for Cellular Growth and Survival: Application to Proliferation and Cytotoxicity Assays*, Journal of Immunological Methods, 1983, vol. 65, pp. 55-63.

Müller A. et al., *Receptor Binding and Internalization of a Water-Soluble (1→3)-β- D-Glucan Biologic Response Modifier in Two Monocyte/Macrophage Cell Lines*, J. Immunol., 1996, vol. 156, pp. 3418-3425.

Murphy, E. et al., *Detection of in vivo expression of interleukin-10 using a semi-quantitative polymerase chain reaction method in Schistosoma mansoni Infected Mice*, Journal of Immunological Methods, 1993, vol. 162, pp. 211-223.

Norkin L. et al., *Association of Caveolin with Chlamydia trachomatis Inclusions at Early and Late Stages of Infection*, Exp. Cell. Res., 2001, vol. 266, pp. 229-238.

Puccetti P. et al., *Use of a skin test assay to determine tumor-specific $CD8^+$ T cell reactivity*, Eur. J. Immuno., 1994, vol. 24, pp. 1446-1452.

Robbins P. et al., *A Mutated β-Catenin Gene Encodes a Melanoma-specific Antigen Recognized by Tumor Infiltrating Lymphocytes*, J. Exp. Med., 1996, vol. 183, pp. 1185-1192.

Sanchez, J. et al., *The mouse Swiss-2D Page database: a tool for proteomics study of diabetes and obesity*, Proteomics, 2001, vol. 1, pp. 136-163.

Shaffer A., *XBP1 , Downstream of Blimp-1, Expands the Secretory Apparatus and Other Organelles, and Increases Protein Synthesis in Plasma Cell Differentiation*, Immunity, 2004, vol. 21, pp. 81-93.

Shao B. et al., *Immune receptors for polysaccharides from Ganoderma lucidum*, Biochem. Biophys. Res, Commun., 2004, vol. 323, pp. 133-141.

Shapiro-Shelef M. et al., *Blimp-1 Is Required for the Formation of Immunoglobulin Secreting Plasma Cells and Pre-Plasma Memory B Cells*, Immunity, 2003, vol. 19, pp. 607-620.

Shiao M. et al., *Natural Products and Biological Activities of the Chinese Medicinal Fungus Ganoderma lucidum*, American Chemical Society, 1994, pp. 342-354.

Sieckmann D. et al., *Activation of Mouse Lymphocytes By Anti-Immunoglobulin*, J. Exp. Med., 1978, vol. 147, pp. 814-829.

Smith J. et al., *Current Protocols in Molecular Biology*, John Wiley & Sons, Inc., 2005, Sec. 11.1-11.3.

Somani B. et al., *A Modified Anthrone-Sulfuric Acid Method for the Determination of Fructose in the Presence of Certain Proteins*, Anal. Biochem., 1987, vol. 167, p. 327-330.

Sone Y. et al. *Structures and Antitumor Activities of the Polysaccharides Isolated from Fruiting Body and the Growing Culture of Mycelium of Ganoderma lucidum*, Agric. Biol. Chem., 1985, vol. 49, pp. 2641-2653.

Spackman D. et al., *Automatic Recording Apparatus for Use in the Chromatography of Amino Acids*, Anal. Chem., 1958, vol. 30, pp. 1190-1206.

Usui, T. et al. *Isolation and characterization of antitumor active β-D-glucans from the fruit bodies of Ganoderma applanatum*, Carbohydrate Research, 1983, vol. 115, pp. 273-280.

Van Strijp J. et al., *Ligand Specificity of Purified Complement Receptor Type Three (CD11b/CD18, $^\alpha m^\beta 2$, Mac-1)*, J. Immunol., 1993, vol. 151, pp. 3324-3336.

Větvička V. et al., *Soluble β-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells*, J. Clin. Invest., 1996, vol. 98, pp. 50-61.

Vitiello a. et al., *Development of a Lipopeptide-based Therapeutic Vaccine to Treat Chronic HBV Infection*, J. Clin. Inv. 1995, vol. 95, pp. 341-349.

Wang S. et al., *The Anti-Tumor Effect of Ganoderma Lucidum is Mediated by Cytokines Released from Activated Macrophages and T. Lymphocytes*, Int. J. Cancer, 1997, vol. 70, pp. 699-705.

Wang Y. et al., *Studies on the Immuno-Modulating and Antitumor Activities of Ganoderma lucidum (Reishi) Polysaccharides: Functional and Proteomic Analyses of a Fucose-Containing Glycoprotein Fraction Responsible for the Activities*, Bioorg. Med. Chem., 2002, vol. 10, pp. 1057-1062.

Widmann C. et al., *T helper epitopes enhance the cytotoxic response of mice immunized with MHC class I-restricted malaria peptides*, J. Immunol. Methods, 1992, vol. 155, pp. 95-99.

York I. et al., *Antigen Processing and Presentation by the Class I Major Histocompatibility Complex*, Annu. Rev. Immunol., 1996, vol. 14, pp. 369-396.

Zhang J. et al., *Activation of B lymphocytes by GLIS, a bioactive proteoglycan from Ganoderma lucidum*, Life Sci., 2002, vol. 71, pp. 623-638.

Asadullah, K. et al., *Interleukin-10 and Psoriasis*, Interleukin-10, 2006, pp. 161-168.

Raj, D. et al., *Keratinocyte Apoptosis in Epidermal Development and Disease*, J. Investigative Dermatology, 2006, vol. 126, pp. 243-257.

\* cited by examiner

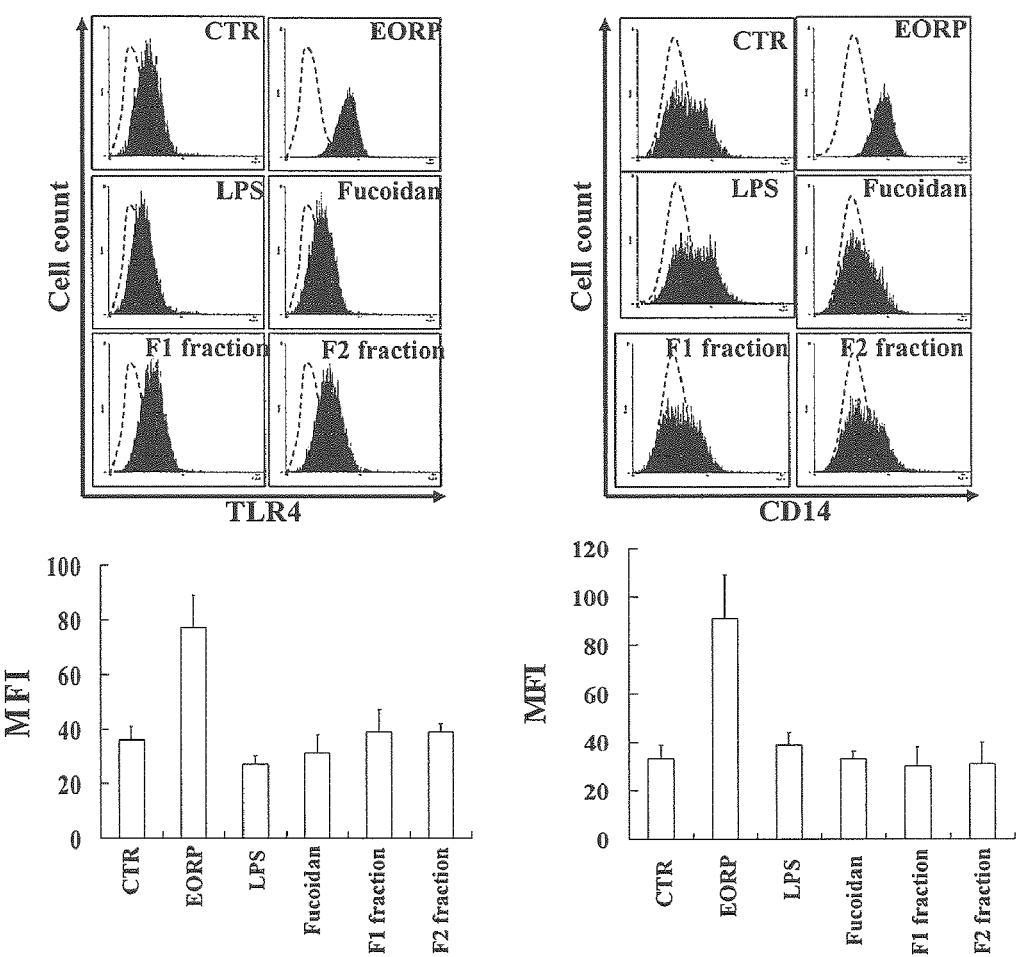

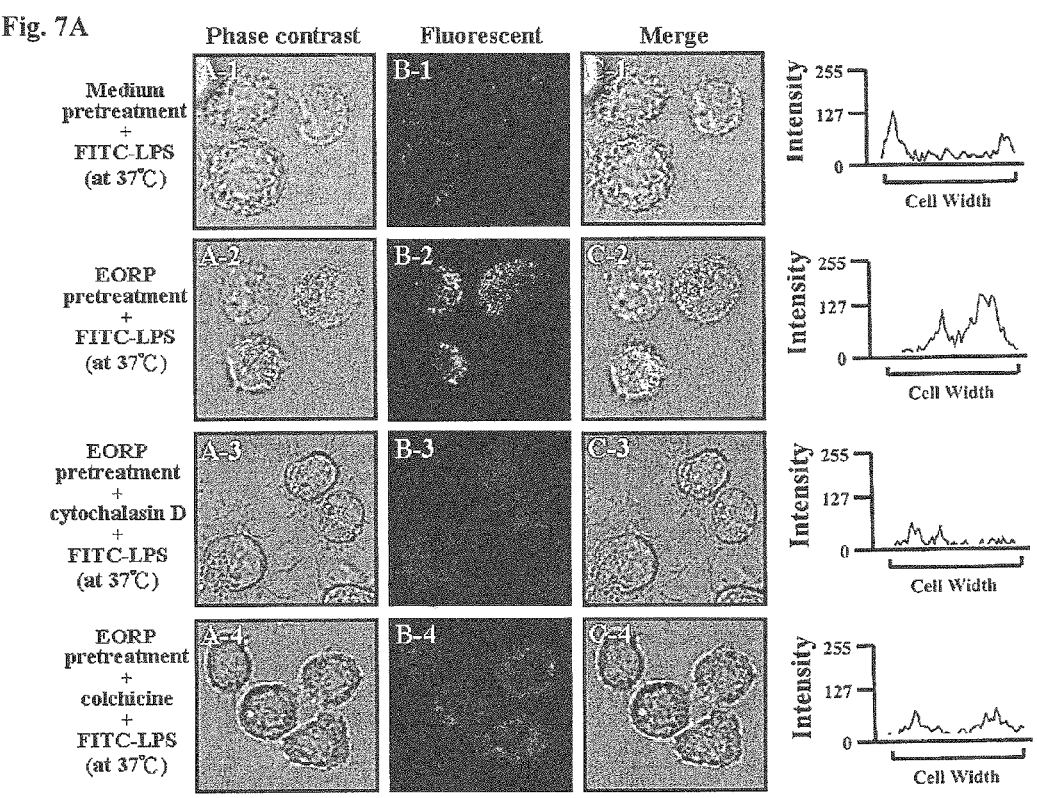

| Sample | 1 | 2 | 3 | 4 | 5 | 6 |
|---|---|---|---|---|---|---|
| Cytochalasin D (µM) | – | – | 1 | 10 | – | – |
| Colchicine (µM) | – | – | – | – | 10 | 30 |
| LPS (6 h) | – | + | + | + | + | + |

| Sample | 1 | 2 | 3 | 4 | 5 | 6 |
|---|---|---|---|---|---|---|
| Cytochalasin D (µM) | – | – | 1 | 10 | – | – |
| Colchicine (µM) | – | – | – | – | 10 | 30 |
| LPS (6 h) | – | + | + | + | + | + |

US 7,687,064 B2

METHODS AND COMPOSITIONS ASSOCIATED WITH ADMINISTRATION OF AN EXTRACT OF *GANODERMA LUCIDUM*

This application is a continuation-in-part of PCT/US2005/36961, filed Oct. 14, 2005 which is a continuation-in-part of U.S. patent application Ser. No. 10/213,257, filed Aug. 6, 2004, now U.S. Pat. No. 7,135,183 which claims the benefit of U.S. Provisional Patent Application Ser. No. 60/310,285, filed Aug. 6, 2001. PCT/US2005/36961 also claims the benefit of U.S. Provisional Patent Application Ser. No. 60/619,263, filed Oct. 14, 2004. The contents of each prior application are specifically incorporated herein by reference in their entirety.

FIELD OF THE DISCLOSURE

The present disclosure refers to the field of immunology and cellular biology.

BACKGROUND OF THE DISCLOSURE

*Ganoderma* species (a group of medical fungus) is known in the art. *Ganoderma lucidum* (Reishi or Ling-Zhi) has been used as traditional Chinese medicine (TCM) for promoting good health, perpetual youth, and longevity and in particular extract of Reishi were used as anti-tumor and immuno-modulating agent. Reishi is also known to exhibit liver protective, hypoglycemic and platelet aggregation-inhibiting activities.

Although the receptor complement receptor type three (CR3) has been shown to bind the β-glucan polysaccharides, the receptor, and carbohydrate epitope responsible for the anti-tumor activity remain to be established.

SUMMARY OF THE DISCLOSURE

In one aspect, the disclosure provides a method for increasing the secretion of IL-1 by a lipopolysaccharide (LPS)-stimulated macrophage, the method comprising administering an effective amount of a fucose-containing glycoprotein fraction from *Ganoderma lucidum* to the macrophage prior to and/or during LPS stimulation.

In another aspect, the disclosure provides a method for increasing the serum level of IL-1 that is produced in response to introduction of lipopolysaccharide (LPS) into a mammal, the method comprising administering an effective amount of a fucose-containing glycoprotein fraction from *Ganoderma lucidum* to the mammal prior to or at the same time as said mammal comes into contact with said LPS.

In another aspect, the disclosure provides a method for increasing the serum level of IL-1 receptor antagonist (IL-1Ra) in a mammal, the method comprising administering an effective amount of a fucose-containing glycoprotein fraction from *Ganoderma lucidum* to the mammal.

In another aspect, the disclosure provides a method for increasing the secretion of IL-1 by a monocyte, the method comprising administering an effective amount of a fucose-containing glycoprotein fraction from *Ganoderma lucidum* to the monocyte.

In another aspect, the disclosure provides a method for increasing the secretion of IL-1Ra by a monocyte, the method comprising administering an effective amount of a fucose-containing glycoprotein fraction from *Ganoderma lucidum* to the monocyte.

In another aspect, the disclosure provides a method for increasing the secretion of IL-1Ra by a macrophage, the method comprising administering an effective amount of a fucose-containing glycoprotein fraction from *Ganoderma lucidum* to the macrophage.

In another aspect, the disclosure provides a method for increasing expression of TLR4 on the surface of a macrophage, the method comprising administering an effective amount of a fucose-containing glycoprotein fraction from *Ganoderma lucidum* to the macrophage.

In another aspect, the disclosure provides a method for increasing expression of CD14 on the surface of macrophage, the method comprising administering an effective amount of a fucose-containing glycoprotein fraction from *Ganoderma lucidum* to the macrophage.

In another aspect, the disclosure provides a method for increasing the uptake and clearance of lipopolysaccharide (LPS) by a LPS-stimulated macrophage, the method comprising administering an effective amount of a fucose-containing glycoprotein fraction from *Ganoderma lucidum* to the macrophage prior to and/or during LPS stimulation.

In another aspect, the disclosure provides a method for increasing lipopolysaccharide (LPS)-stimulated activation of at least one of ERK, JNK, and p38 in a macrophage, the method comprising administering a fucose-containing glycoprotein fraction from *Ganoderma lucidum* to the macrophage prior to and/or during LPS stimulation.

The aforementioned methods are useful for enhancing the response of the innate immunity system to bacterial pathogens, particularly to Gram-negative bacterial pathogens. The methods may be used prophylactically or therapeutically using pharmaceutical compositions that comprise a fucose-containing glycoprotein fraction from *Ganoderma lucidum*.

BRIEF DESCRIPTION OF THE DRAWINGS

The above-mentioned features and objects of the present disclosure will become more apparent with reference to the following description taken in conjunction with the accompanying drawings wherein like reference denote like elements and in which:

FIG. 1 illustrates that F3 increases surface expression of TLR4 and CD14 within J774A.1 cells. In FIG. 1A, J774A.1 cells were incubated with one of F3 (25 µg/mL), LPS (1 µg/mL), fucoidan (25 µg/mL), F1 fraction of Reishi (25 µg/mL) or F2 fraction of Reishi (25 µg/mL) for 24 h, fixed with 2% paraformaldehyde, followed by stained with PE-conjugated TLR4 or CD14 antibody for 30 min, then analyzed by flow cytometry. Dotted line: isotype control antibody; shade histograms: treatment as indicated. The histograms were quantified and represent as mean fluorescence intensity (MFI).

FIG. 2 shows that F3 increases LPS binding and internalization by J774A.1 cells.

FIG. 3 shows that F3 promotes co-localization of internalized LPS with lysosome and Golgi apparatus markers.

FIG. 4 shows that F3 pretreatment increases IL-1 and IL-1Ra secretion from LPS-stimulated human primary macrophages, J774A.1 cells and mice.

FIG. 5 shows that pretreatment of J774A.1 cells with F3 increases LPS-induced IL-1 gene expression.

FIG. 6 shows that F3 pretreatment up-regulates LPS-induced proIL-1/IL-1 expression via activation of mitogen activated protein kinases (MAPKs).

FIG. 7 shows that inhibitors of endocytosis reduce LPS internalization by J774A.1 cells but not LPS dependent activation. In FIG. 7A, J774A.1 cells were pretreated with F3 (25 μg/mL) for 24 h, then washed with PBS, and treated with cytochalasin D (10 μM), colchicines (30 μM) or vehicle control (DMSO) for 30 min, followed by FITC-LPS (green) treatment at 37° C. for 1 h. After fixation, cells were examined under confocal microscope.

DETAILED DESCRIPTION OF THE EMBODIMENTS

General Description of Reishi

Figure 1B:
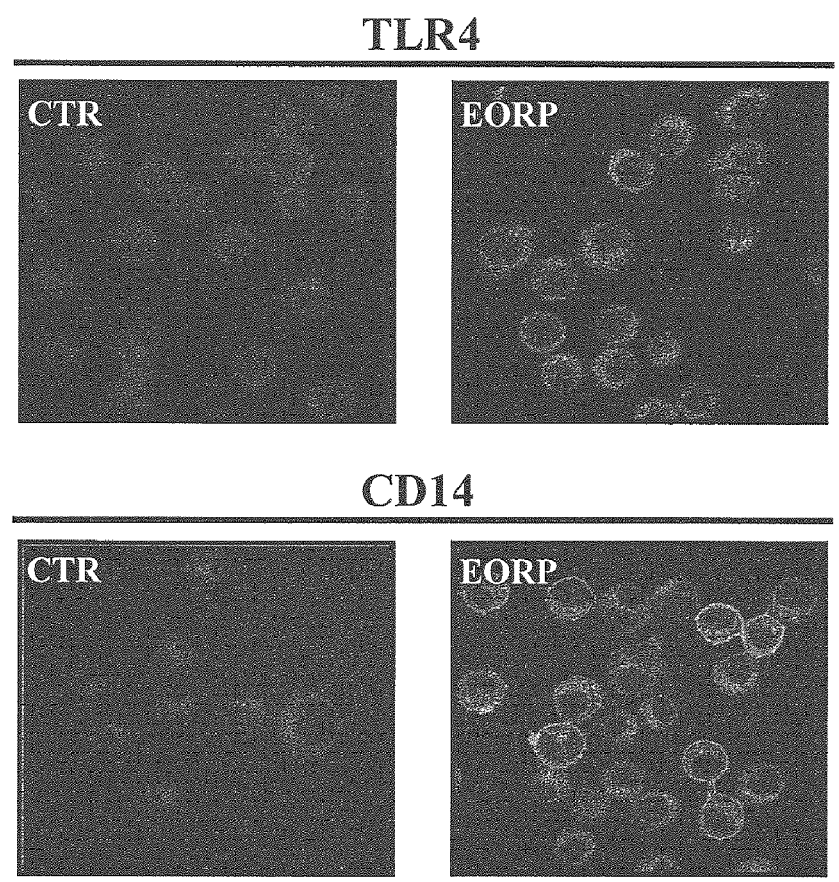
In FIG. 1B, J774A.1 cells were incubated with medium or F3 (25 µg/mL) for 24 h, followed by stained with PE-conjugated TLR4 or CD14 antibody, then analyzed by confocal microscope. Note that EORP=F3.

According to one aspect, a fucose-containing glycoproteic fraction of an extract of *Ganoderma Lucidum* Reishi, is disclosed. The phrase "fucose-containing glycoprotein fraction"

refers to a constituent part of the extract that includes at least one of a polysaccharide and a glycopeptide comprising fucose residues.

The term "glycoprotein" or "glycopeptide" refers to a protein of any length and dimensions with covalently attached sugar units, either bonded via the OH group of serine or threonine O glycosylated) or through the amide $NH_2$ of asparagine (N-glycosylated) or portions thereof. The term "polysaccharide" refers to a polymers of any length and dimensions comprising monosaccharide residues linked glycosidically in branched or unbranched chains.

The term "extract" refers to a concentrated preparation obtained by removing active constituents from a given substance; when the active constituents are included in a solvent, the removal of the active constituents can be performed by evaporating all or nearly all the solvent and adjusting the residual mass or powder to a prescribed standard; extracts are usually prepared in three forms, semiliquid or of syrupy consistency, pilular or solid and as dry powder. The phrase "Ganoderma Lucidum" refers to fungus Ganoderma Lucidum or Reishi, any tissue, part or fraction therefrom and/or any preparation thereof including homogenates, suspensions, filtrates, filtration residues and solutions. The term "preparation" refers to a composition processed, manufactured, or compounded starting from a given substance, the term "concentrated preparation" refers to a preparation with an increased ratio of the mass or volume of active constituents to the mass or volume of the non-active constituents or to the mass volume of the entire composition, compared with the same ratio in the given substance. The term "fraction" refers to one of the separable constituents of a substance.

In some embodiments, the fucose-containing glycoprotein fraction is included in a fraction of Ganoderma Lucidum (herein also denominated F3, Fraction 3, EORP, GL(PS)_Wu, or Wu) showing a light absorbance of about 1.8 O.D. at 625 nm identified and isolated from a water-soluble extract of Ganoderma Lucidum (crude Reishi extract) by experimental procedures exemplified in Example 1, 2 and 3.

Fraction 3 includes a fucose-containing glycoprotein fraction, which comprises terminal fucose residues. The phrase "terminal fucose residues" identifies fucose residues of a chain of sugars located in a region proximate to a free end of a chain of sugars. The fucose-containing glycoprotein fraction of Fraction 3, also includes fucose residues bound with $\alpha 1,2$-fucosidic linkages and $\alpha 3,4$-fucosidic linkages.

In addition to fucose residue, fucose-containing glycoprotein fraction of Fraction 3 can also comprise glucose mannose, N-acetylglucosamine, xylose and rhamnose, as established by experimental procedures exemplified in Example 1 and Example 2.

The fucose-containing glycoprotein fraction of Fraction 3 can also include an amino acidic component, as established by experimental procedures exemplified in Example 1. The amino acidic component of Fraction 3, however, can be significantly modified without impairing the activities associated with the fucose-containing glycoprotein fraction of Fraction 3.

Fraction F3 can be obtained by a process comprising: homogenizing a plant tissue of Ganoderma Lucidum and/or providing an homogenized plant tissue from Ganoderma Lucidum; extracting the homogenized plant tissue of Ganoderma Lucidum; and filtering the extracted homogenized plant tissue to form one or more fractions, the fractions comprising a saccharide component having fucose residues. The fractions formed in the above procedures can also be treated with protease.

The term "extracting" refers to any suitable procedure or protcol to provide an extract starting from a given substance; determination of such protocols can be accomplished by those skilled in the art depending upon a variety of variables, including the substance and the active constituents to be removed from the substance; exemplary procedures include treatment based on different solubility of the constituents of the substance in different solvents. Extracting the homogenized plant tissue can be performed by any suitable procedure or protocol to provide an extract of Ganoderma Lucium including a fucose-containing glycoprotein or fucose-containing polysaccharide constituents from the homogenized plant tissue; for example a suitable procedure includes treating the homogenized plant tissue with aqueous alkalyne solution, for example 0.1 N NaOH, for a predetermined time to form a crude extract.

The term "filtering" or "filtration" refers to any suitable procedure to separate a constituent of a substance, such as an active constituent, from other constituents of the substance, such as impurities; determination of such protocols can be accomplished by those skilled in the art depending upon a variety of variables, including the substance, the active constituents and the inactive constituents of the substance; exemplary filtration procedures include dialysis and gel filtration chromatography. Filtering the extracted homogenized plant tissue can be performed by subjecting the crude extract to filtration, such as gel filtration chromatography e.g. using a Sephacryl S-500 column, and eluting with an aqueous solution to form one or more fractions. In one embodiment the aqueous solution is buffered at about pH 7.0, for example a Tris buffer solution.

Specific embodiments of the above-mentioned process to obtain Fraction 3 are exemplified in Examples 1, 2 and 3.

In additional embodiments the fucose-containing glycoprotein fraction is included in fractions of Fraction F3 (herein also collectively named Subfractions), herein identified as F3G1, F3G2, F3G3, and the F3G2 sub-fractions F3G2H1 and F3G2H2. The Subfractions are isolated from Fraction 3 by experimental procedures exemplified in Example 2. Hence, the term "fucose-containing glycoprotein" refers not only to Fraction F3, but also to any Subfractions thereof, and any combination of F3 with the Subfractions, or any combination of the Subfractions.

The different Subfractions can be identified by the respective ability to absorb light. F3G1 shows a light absorbance of about 0.4 O.D. at 480 nm, F3G2 shows a light absorbance of about 0.1 O.D. at 480 nm; F3G2H1 shows a light absorbance of about 0.10 O.D. at 480 nm and F3G2H2 shows a light absorbance of about 0.5 O.D. at 480 nm, as established by experimental procedures exemplified in Example 2.

F3 and the Subfractions are also herein collectively named Fractions.

The fucose-containing glycoprotein fraction comprised in the Subfractions can also include in addition to the fucose residues other sugars such as glucose and mannose galactose, N-acetylglucosamine, and xylose as established by experimental procedures exemplified in Example 2 (see in particular Table IV).

The Subfractions F3G1, FG2 and F3G3 can be obtained by partitioning Fraction 3. The term "partitioning" refers to any suitable procedure or protocol to divide a substance in two or more constituents thereof; determination of such protocols can be accomplished by those skilled in the art depending upon a variety of variables, including the substance, and the constituents to be partitioned. Partitioning Fraction 3 can be performed by filtering Fraction 3, (for example with an anion exchanger such as Diaion-WA30 anion exchanger or by gel filtration chromatography, e.g. on a TSK HW-75 column), and isolating the Subfractions F3G1, F3G2 and F3G3 from the filtered Fraction 3, (for example by elution with an alkaline solution, including for example at least one of NaCl).

F3G2 subfractions F3G2H1 ad F3G2H2 can be obtained by subjecting F3G2 to further partitioning. For example, partitioning of F3G2 can be performed by filtering Sub-fraction F3G2 e.g. by gel filtration chromatography e.g. on a TSK HW-75 column, and isolating the Subfractions F3G2H1 and F3G2H2 from the filtered Subfraction F3G2 e.g. by eluting the filtered Subfraction F3G2 with an aqueous solution.

Exemplary embodiments of the above-mentioned process to obtain the Subfractions are illustrated in Example 2.

The term "effective amount" of a compound is at least the minimum amount of the compound that is necessary to minimally achieve, and more preferably, optimally achieve, the desired effect. An effective amount of fucose-containing glycoprotein fraction for use in a given method can be readily determined by one skilled in the art without undue experimentation, depending upon the particular circumstances encountered (e.g. concentrations, cell type and number, etc.) upon reading of the present disclosure and in particular the Examples section.

The term "administering" refers to any process or protocol suitable to put a compound, and in particular the fucose-containing glycoprotein fraction, in contact with the cell, wherein the term "contact" or the phrase "put in contact" mean to place the compound and in particular the fucose-containing glycoprotein fraction and the cell, in a mutual spatial relationship such that a biological interaction between the compound and the cell is feasible; the phrase "biological interaction" refers to the process by which a compound and in particular the fucose-containing glycoprotein fraction controls, influences or otherwise affects the normal functioning and/or survival of the cell; determination of such protocols can be accomplished by those skilled in the art depending upon a variety of variables, including the type of cell, whether the contact occurs in vitro, in vivo or ex vivo. Acceptable protocols to administer the fucose-containing glycoprotein fraction include individual dose size, number of doses, frequency of dose administration, and mode of administration, such as topical administration, local administration, or oral administration in vivo, incubation and assays in vitro, or ex vivo administration e.g. to isolated hematopoietic cells, which can be identified by a person skilled in the art upon reading of the present disclosure and, in particular, the Examples section.

In one embodiment, the fucose-containing glycoprotein fraction is used in a method to increase in a lipopolysaccharide (LPS)-stimulated macrophage any of: the expression of the pro-IL-1 gene in the macrophage and/or processsing of pro-IL-1 protein to IL-1 in the macrophage and/or the secretion of IL-1 by the macrophage. The method involves administering an effective amount of the fucose-containing glycoprotein fraction to a macrophage prior to and/or during LPS stimulation. In such a method, the level of IL-1 secreted and/or the level of pro-IL-1 protein and/or the level of pro-IL-1 gene expression (for example, as measured by the level of pro-IL-1 mRNA produced) in macrophage that is treated with the fucose-containing glycoprotein fraction prior to LPS stimulation exceeds the levels exhibited by a LPS-stimulated macrophage that has not been treated with the fucose-containing glycoprotein fraction. See Examples 7-9. As is appreciated in the art, LPS is an endotoxin found on the surface of Gram-negative bacterial cells, and is a potent stimulator of the normal immune response within certain monocytes and macrophages [73]. LPS-binding protein catalyzes the transfer of LPS to plasma membranes or to soluble CD14, which in turn mediates the recognition of LPS through TLR4 [74], leading to the transduction of the multiple signals involved in the normal anti-bacterial response, including the production of cytokines, such as IL-1 [76]. As is appreciated in the art, the IL-1 cytokine is a potent inflammatory cytokine that is produced as a precursor form, pro-IL-1, then cleaved into the 17-kD secreted mature form by interleukin 1 converting enzyme (ICE) [84-85]. It is known in the art that mice pretreated with recombinant IL-1 prior to infection with *E. coli* have significantly lower mortality rates compared with untreated mice [87]. Accordingly, the discovery that the administration of the fucose-containing glycoprotein fraction to macrophages increases the expression and secretion of IL-1 that occurs in response to LPS stimulation indicates that the methods and compositions of the disclosure will be useful as therapeutics for the treatment and prevention of bacterial infections.

According to another aspect, a method to increase the serum level of IL-1 that is produced in response to introduction of LPS into a mammal is disclosed. The method involves administering an effective amount of the fucose-containing glycoprotein fraction to a mammal prior to and/or during contact of the mammal with LPS. The level of IL-1 in the serum of a mammal following administration of LPS is higher if the mammal is pretreated with the fucose-containing glycoprotein fraction prior to coming into contact with LPS than if the mammal is not pretreated with the fucose-containing glycoprotein fraction prior to coming into contact with LPS. See Example 8.

According to another aspect, a method to increase the serum level of IL-1 receptor antagonist (IL-1Ra) in a mammal is disclosed. The method involves administering an effective amount of the fucose-containing glycoprotein fraction to a mammal. As is appreciated by those skilled in the art, IL-1Ra is a member of the IL-1 superfamily and competes with IL-1 for binding to IL-1 receptor (IL-1R), but does not induce any intracellular response compared to IL-1 stimulation [90]. As disclosed above and in the Example below, the LPS-induced serum level of IL-1 is higher in a mammal that is pretreated with the fucose-containing glycoprotein fraction prior to coming into contact with LPS, than in a mammal that is not pretreated with the fucose-containing glycoprotein fraction; however, the increased serum level of IL-1 is not associated with toxic events that are believed to result from excessive levels of IL-1 in the circulation system of a mammal. High systemic levels of IL-1 are known to be associated with shock and organ failure associated with sepsis and joint inflammation associated with rheumatoid arthritis [88-89]. Without being limited by a theory or mechanism, it is believed that the increase in serum levels of IL-1Ra induced by the fucose-containing glycoprotein fraction preserves the access of IL-1 to IL-1 receptor when the innate immunity system of the mammal comes into contact with LPS. Accordingly, it is believed that the induction of IL-1Ra by the fucose-containing glycoprotein fraction protects the mammal from the potentially toxic effects of high systemic levels of IL-1. See Example 8. Hence, the methods provided herein are useful for the treatment or prevention of bacterial infection and will avoid the cytotoxic effects of high systemic levels of IL-1.

According to another aspect, a method to increase the secretion of IL-1 by a monocyte is disclosed. The method involves administering an effective amount of the fucose-containing glycoprotein fraction to a monocyte. See Example 8.

According to another aspect, a method to increase the secretion of IL-1Ra by a monocyte is disclosed. The method involves administering an effective amount of the fucose-containing glycoprotein fraction to a monocyte. See Example 8.

According to another aspect, a method to increase the secretion of IL-1Ra by a macrophage is disclosed. The method involves administering an effective amount of the fucose-containing glycoprotein fraction to a macrophage. See Example 8.

According to another aspect, a method to increase expression of TLR4 on the surface of a macrophage is disclosed. The method involves administering an effective amount of the fucose-containing glycoprotein fraction to a macrophage. While not being limited by theory or mechanism, it is believed that the increase in TLR4 expression on the surface of macrophages leads to an increase in TLR4-mediated signalling via activation of mitogen activated protein kinases (MAPKs) upon exposure of the macrophage to LPS. This in turn is believed to lead to the observed increases in IL-1 gene expression, pro-IL-1 production, and IL-1 secretion by the macrophage. See Example 4.

According to another aspect, a method for increasing expression of CD14 on the surface of macrophage is disclosed. The method involves administering an effective amount of the fucose-containing glycoprotein fraction to a macrophage. See Example 4.

According to another aspect, a method for increasing the uptake and clearance of LPS by a LPS-stimulated macrophage is disclosed. The method involves administering an effective amount of the fucose-containing glycoprotein fraction to a macrophage prior to and/or during LPS stimulation. Without being limited by theory or mechanism, it is believed that the fucose-containing glycoprotein fraction increases the surface expression of CD14, which serves as a cell surface receptor for LPS. In addition, without being limited by theory or mechanism, it is believed that the fucose-containing glycoprotein fraction also enhances the binding of LPS to CD14, which again contributes to the increase in surface bound LPS seen in the presence of the fucose-containing glycoprotein fraction. See Example 5. In addition, without being limited by theory or mechanism, it is believed that the fucose-containing glycoprotein fraction promotes the co-localization of internalized LPS with the lysosome. See Example 6.

It will be appreciated by those skilled in the art that the uptake by phagocytosis of certain bacteria and bacterial components (such as LPS) by macrophages, followed by the clearance of those components within the macrophage (e.g. within the acidic lysosome) plays a crucial role in the response of the innate immunity system to bacterial infections [102]. Accordingly, one skilled in the art will appreciate that the methods disclosed herein, by increasing uptake and clearance of LPS by macrophages, and by increasing the secretion of the inflammatory cytokine IL-1, will therefore enhance the response of the innate immunity system to bacterial infections. Thus, the methods and compositions disclosed herein may be used prophylactically to prevent bacterial infection, or they may be used therapeutically to treat a bacterial infection. In particular, the methods and compositions disclosed herein may be used to treat or prevent infection by Gram-negative bacteria, including, but not limited to, *Escherichia coli, Salmonella* spp., *Shigella* spp., *Neisseria* spp., *Vibrio cholerae, Rickettsia* spp., *Chlamydia* spp., *Mycoplasma pneumoniae, Treponema pallidum*, and *Borellia burgdorferi*.

It has been discovered by the present inventors that phosphorylation of ERK, JNK, and p38 in macrophages stimulated with LPS increases if the macrophage is pretreated with the fucose-containing glycoprotein fraction prior to stimulation with LPS. See Example 10. Accordingly, in another aspect, a method of increasing LPS-stimulated activation of at least one of ERK, JNK, and p38 in a macrophage is disclosed. The method comprises administering the fucose-containing glycoprotein fraction to a macrophage prior to and/or during LPS stimulation. Without being limited by a theory or mechanism, it is believed that the increase in LPS-stimulated activation of JNK and p38 observed in macrophages pretreated with the fucose-containing glycoprotein fraction leads to an increase in the level of pro-IL-1 expression, and consequently in the level of IL-1 secreted by the macrophage. See Example 11.

Note that in all of the foregoing, the administration of the fucose-containing glycoprotein fraction to a mammalian cell, such as a human macrophage or monocyte, can occur ex vivo or in vivo.

Pharmaceutical Compositions

According to another aspect, the fucose-containing glycoprotein fraction can be included in a pharmaceutical composition together with additional active agents, carriers, vehicles, excipients or auxiliary agents identifiable by a person skilled in the art upon reading of the present disclosure.

The pharmaceutical compositions preferably comprise at least one pharmaceutically acceptable carrier. In such pharmaceutical compositions, the fucose-containing glycoprotein forms the "active compound," also referred to as the "active agent." As used herein the language "pharmaceutically acceptable carrier" includes solvents, dispersion media, coatings, antibacterial and antifungal agents, is 6 tonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Subject as used herein refers to humans and non-human primates (e.g. guerilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer) and any other organisms who can benefit from the agents of the present disclosure. There is no limitation on the type of animal that could benefit from the presently described agents. The most preferred subject of the present disclosure is a human. A subject regardless of whether it is a human or non-human organism may be referred to as a patient, individual, animal, host or recipient.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of the active compound (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors can influence the dosage and timing required to effectively treat a subject, including but not limited to the severity of the disease or disorder, previous treatments, the general health and/or age of the subject, and other diseases present.

EXAMPLES

The present disclosure is further described by the following non-limiting examples.

Material and methods and statistical analysis used in the following Examples 1-3 are described in Wong et al. 2002, Hsu et al 2004; Chien et al, 2004 and Chen et al. 2004 each of them herein incorporated by reference in its entirety.

Example 1

Preparation and Analysis of Reishi Extracts F1, F2, F3, F4, and F5

Crude Reishi extract (prepared via alkaline extraction (0.1 N NaOH), neutralization and ethanol precipitation) was obtained from Pharmanex Co. (CA, USA). Twenty-eight mg of the crude extract were dissolved in 2 mL of Tris buffer (pH 7.0, 0.1 N) and centrifuged to remove the insoluble materials (7 mg). The supernatant was purified by gel filtration chromatography using a Sephacryl S-500 column (100×1.6 cm) with 0.1 N Tris buffer (pH 7.0) as the eluent. The flow rate was set at 0.5 mL/min, and the elute (7.5 mL per tube) was collected. Five fractions were collected (fractions 1-5), each dialyzed to remove excessive salt and lyophilized to give 1.0 mg, 6.2 mg, 5.3 mg, 2.1 mg, and less than 1 mg, respectively.

Fractions 1 to Fractions 5 are identifiable as it follows: Fraction 1: 100-130 mL; Fraction 2: 130-155 mL; Fraction 3: 155-205 mL; Fraction 4: 205-220 mL; Fraction 5: 220-255 mL.

The main fraction having a light absorbance of about 1.8 at O.D. 625 was designated as Fraction 3. After the chromatography, the crude extract and each of the isolated fraction were subjected to anthrone analysis (Somani et al 1987; Jarmyn 1975; Halhoul and I. Kleinberg 1972) to detect sugar components.

Sugar Composition Analysis: Anthrone Colorimetric Method

Each 1.5 mL of anthrone (9,10-dihydro-9-oxoanthracene) solution (0.2 g anthrone dissolved in 100 mL of concd sulfuric acid) in a series of test tubes immersed in an ice water bath was carefully overlayed with 1.5 mL of sample (20-40 µg/mL of -glucose or equivalent). After all additions had been made, the tubes were shaken rapidly and then replaced in an ice water bath. The tubes were heated for 5 min in a boiling water bath and then cooled; the optical densities were read within an hour at 625 nm against distilled water. Standards, reagent blanks and unknowns were run in triplicate because of likely contamination by other carbohydrate sources. Calculations made on the basis that the optical densities are directly proportional to the carbohydrate concentration.

Sugar Composition Analysis-TMS Method

For monosaccharide analysis, the polysaccharide extracts/fractions were methanolyzed with 0.5 M methanolic-HCl (Supelco) at 80° C. for 16 h, re-N-acetylated with 500 µL of methanol, 10 µL of pyridine and 50 µL of acetic anhydride, and then treated with the Sylon HTP® trimethylsilylating reagent (Supelco) for 20 min at room temperature, dried and redissolved in hexane. GC-MS analysis of the trimethylsilylated derivatives was carried out using a Hewlett-Packard (HP) Gas Chromatograph 6890 connected to a HP 5973 Mass Selective Detector. Samples were dissolved in hexane prior to splitless injection into a HP-5MS fused silica capillary column (30 m×0.25 mm I.D., HP). The column head pressure was maintained at around 8.2 psi to give a constant flow rate of 1 mL/min using helium as carrier gas. Initial oven temperature was held at 60° C. for 1 min, increased to 140° C. at 25 C/min, to 250° C. at 5° C./min, and then increased to 300° C. at 10° C./min.

The carbohydrate composition of crude extract is reported in Table I, the carbohydrate composition of Fraction 3 is reported in Table II, below.

TABLE I

Carbohydrate compositions of crude Reishi extract

| Sugar components | Percentage (%) |
|---|---|
| D-Glucose | 58.0 |
| D-Mannose | 15.5 |
| L-Fucose | 9.7 |
| D-Galactose | 9.3 |
| D-Xylose | 5.4 |
| D-GlcNAc | 1.0 |
| L-Rhamnose | 0.5 |

TABLE II

Carbohydrate compositions of Fraction 3

| Sugar components | Percentage (%) |
|---|---|
| D-Glucose | 58.1 |
| D-Mannose | 15.1 |
| L-Fucose | 7.1 |
| D-Galactose | 13.5 |
| D-Xylose | 3.1 |
| D-GlcNAc | 1.2 |
| L-Rhamnose | 0.7 |

High-pH anion-exchange chromatography with pulsed amperometric detection (HPAEC/PAD) analysis, confirmed that F3 includes a glycoprotein or polysaccharide comprising fucose residues.

Also $H_2SO_4$/phenol analysis showed that overall polysaccharides concentration in F3 (85%) is higher than crude extract (60%).

Amino Acid Composition Analysis

The analysis was carried out based on a well-established method (Spachman et al 1958; Lo et al 1990). A sample of crude Reishi extract (6 mg) was dissolved in 1 mL solution of 6 M HCl and TFA (4/1), and heated at 140° C. for 3 h. The mixture was concentrated to give a dry residue and dissolved in 100 µL citrate buffer. A small aliquot (4 µL) was withdrawn and subjected to composition analysis by amino acid analyzer (Jeol JLC-6AH).

The resulting amino acid composition of Reishi Crude extract is shown in Table III below.

TABLE III

Amino acid analysis of Reishi extract

| Amino acid | Relative abundance |
|---|---|
| Asp | 117 |
| Thr | 66 |
| Ser | 54 |
| Glu | 120 |
| Pro | 60 |
| Gly | 108 |
| Ala | 100 |
| Val | 61 |
| Met | 6 |
| Ile | 36 |
| Leu | 55 |
| Tyr | 16 |

TABLE III-continued

Amino acid analysis of Reishi extract

| Amino acid | Relative abundance |
|---|---|
| Phe | 28 |
| His | 12 |
| Lys | 21 |
| Arg | 22 |

Analysis directed to investigate protein concentration in Reishi cride extract and in Fraction 3 showed a F3 (~10%), crude extract (~20%) in Lowey method with BSA as a standard.

Further indications concerning F3 composition, differences with composition of crude reishi extract and procedures to obtain F3 can be found in Chen et al. 2004 herein incorporated in its entirety.

Example 2

Preparation and Purification of Reishi Extracts F3-F3G1 FRG2, F3 GH1, and F3 GH2

Crude Reishi extract (prepared via alkaline extraction (0.1 N NaOH), neutralization and ethanol precipitation) was obtained from Pharmanex Co., (CA, USA). All the chemicals and reagents were from Sigma Co., (St. Louis, Mo., USA) unless indicated.

Crude Reishi extract (100 g) was dissolved in 3 L of double distilled water, stirred at 4° C. for 24 h, and centrifuged for 1 h to remove the insoluble. The resulting solution was concentrated at 35° C. to give a small volume and lyophilized to generate 70 g powder of dark-brown color, 2.5 g of which were dissolved in a small volume of Tris buffer (pH 7.0, 0.1 N), and purified by gel filtration chromatography using a Sephacryl S-500 column (95×2.6 cm) with 0.1 N Tris buffer (pH 7.0) as the eluent. The flow rate was set at 0.6 mL/min, and 7.5 mL per tube was collected. After the chromatography, each fraction was subjected to anthrone analysis or the phenol-sulfuric acid method as described in Example 1 above, to detect sugar components. Five fractions were collected (fractions 1-5), each dialyzed to remove excessive salt and lyophilized, to give 450 mg of each fraction and in particular of F3.

F3 was further subjected to a column of Diaion-WA30 anion exchanger (Cl⁻ form, 40×3.5 cm) eluted with 0.2 and 0.8 M NaCl at a flow rate of 0.5 mL/min, and two fractions were designated as F3G1 (11% yield based on F3) and F3G2 (10% yield based on F3), respectively. Another fraction (F3G3, 11% yield based on F3) was generated when the column was further eluted with 2 M NaOH.

The carbohydrate composition of the F3G1, F3G2 and F3G3 was determined by anthrone colorimetric method and TMS method. The results are shown in Table IV below.

TABLE IV

Carbohydrate compositions of F3, F3G1, F3G2, and F3G3

Percentage (%)

| | L-Fuc | D-Xyl | D-Man | D-Gal | D-GlcNAc | D-Glc | Unknown |
|---|---|---|---|---|---|---|---|
| F3 | 7.1 | 3.1 | 15.1 | 13.5 | 1.20 | 58.1 | 1.90 |
| F3G1 | 8.0 | 5.7 | 10.2 | 12.6 | 0.25 | 63.2 | 0.05 |
| F3G2 | 6.2 | 4.5 | 18.3 | 5.3 | 0.78 | 64.9 | 0.02 |
| F3G3 | 8.4 | 7.2 | 14.5 | 2.9 | 1.18 | 65.7 | 0.12 |

The results show that both Fraction 3 and the subfractions F3G1, F3G2 and F3G3 comprise glucose and mannose as major components together with smaller amounts of other sugars, including fucose N-acetylglucosamine, xylose and rhamnose, The percentage of galactose is apparently less in F3G2 and F3G3 than in other fractions.

Gel-filtration chromatography of F3G2 was carried out on a TSK HW-75 column (130×2.6 cm) eluted with double distilled water at a flow rate of 0.5 mL/min. Two fractions were collected; F3G2H1 (19% yield based on F3G2) and F3G2H2 (69% yield based on F3G2).

Further indications concerning the composition of F3G1, F3G2, F3G3, F3G2H1 and F3G2H2 and procedures to obtain the Subfractions can be found in Chen et al. 2004, herein incorporated in its entirety.

Example 3

Preparation of Reishi Extract Fraction 3

A crude *G. Lucidum* PS extract prepared via alkaline extraction with 0.1 N of NaOH, followed by neutralization and ethanol precipitation, was obtained from Pharmanex (CA). The crude *G. Lucidum* extract (100 g) was dissolved in 3 L of double-distilled H$_2$O and stirred at 4° C. for 24 h. The solution was centrifuged (16,000 g) at 4° C. for 1 h, and the supernatant was concentrated at 35° C. The slurry product was then lyophilized to obtain 70 g of water-soluble dark brown *G. Lucidum* extract. The extract (2.5 g) was fractionated on Sephacryl S-500 column (95 2.6 cm) with 0.1 N of Tris buffer (pH 7.0) as the eluent. The flow rate was set at 0.6 ml/min, and fractions were collected with 7.5 ml per tube. Five fractions were collected, and each was dialyzed to remove excessive salts and lyophilized to give fractions 1-5; each fraction was characterized, as described in Example 1. The fucose-containing glycoprotein fraction (20~30% yield), i.e., Fraction 3 or F3, was isolated.

To avoid LPS contamination the crude *G. Lucidum* materials and PS extracts were prepared, from growth to harvest, as GMP grade from Pharmanex and the possible bacterial contamination was carefully monitored to meet the Food and Drug Administration standard. The reagents and utensils for preparation of F3 were either endotoxin-free grade or washed with PBS containing 50 μg/ml polymyxin B (PMB), then rinsed with PBS. F3 contained <1 ng of LPS/25 μg, as measured by LAL assay (Sigma-Aldrich). In addition, certain reagents were routinely checked by LAL for examination of LPS contamination.

An additional procedure was performed as described in Wang et al 2002 herein incorporated by reference in its entirety. According to a modified version of the procedure described in Want et al. 2002 comprises, direct centrifugation, isolated polysaccharide from water soluble Reishi sample which showed components as well as F3.

The procedure as below: The water soluble polysaccharide from crude powder of Reishi 1 g was centrifuged (5000 r.p.m., 2800 g) at 4° C. for 1 h to separate polysaccharide by centrifugal filter with MWCO: 100K, the polysaccharide fraction was collected and lyophilized to give F3 (F3>100K) 172 mg (17%). This portion of polysaccharide shown familiar HPLC profile with F3 and its bio-function assay was analyzed, such as effect of proliferation and cytokines release to mice splenocyte, as well as previously F3 function.

Example 4

F3 Increases Macrophage-Membrane Surface Expression of TLR4 and CD14

Using flow cytometry analysis, F3 was observed to specifically up-regulate cell surface expression of TLR4 in cultured murine macrophages (J774A.1) as indicated by mean fluorescence intensity (MFI) (FIG. 1A, left panel), although this is not the case for any of the other Reishi polysaccharide F3-relevant fractions (e.g., fractions 1 and 2, F1 and F2 [69]), nor is it the case for fucoidan, a principal fucose polysaccharide sulphate ester found in brown seaweeds, *Phaeophyceae* species [94]. By contrast, it has been found that LPS treatment down-regulates J774A.1 cells surface expression of TLR4 (FIG. 1A, left panel), an observation, which is similar to that, reported in another LPS tolerance study featuring cultured murine macrophage cells RAW264.7 [95]. In the following investigation, whilst examining the cell membrane expression of CD14, which involved, importantly, LPS-mediated signaling, it has been found that F3 significantly increases CD14 surface expression (FIG. 1A, right panel); but that there was no such analogous effect of LPS, F1, F2 and fucoidan upon CD14 expression. Moreover, using confocal microscopy, it has been further confirmed that only F3, and no other above-mentioned polysaccharides, is able to increase the surface expression of TLR4 and of CD14 by J774A.1 cells (FIG. 1B). In addition, MSR is considered to be a binding receptor of LPS [80], yet interestingly, it has been found that F3 decreases J774A.1 cell surface expression of MSR, however, LPS was also observed to up-regulate J774A.1 cell surface expression of MSR (data not shown).

Example 5

Figure 2A:
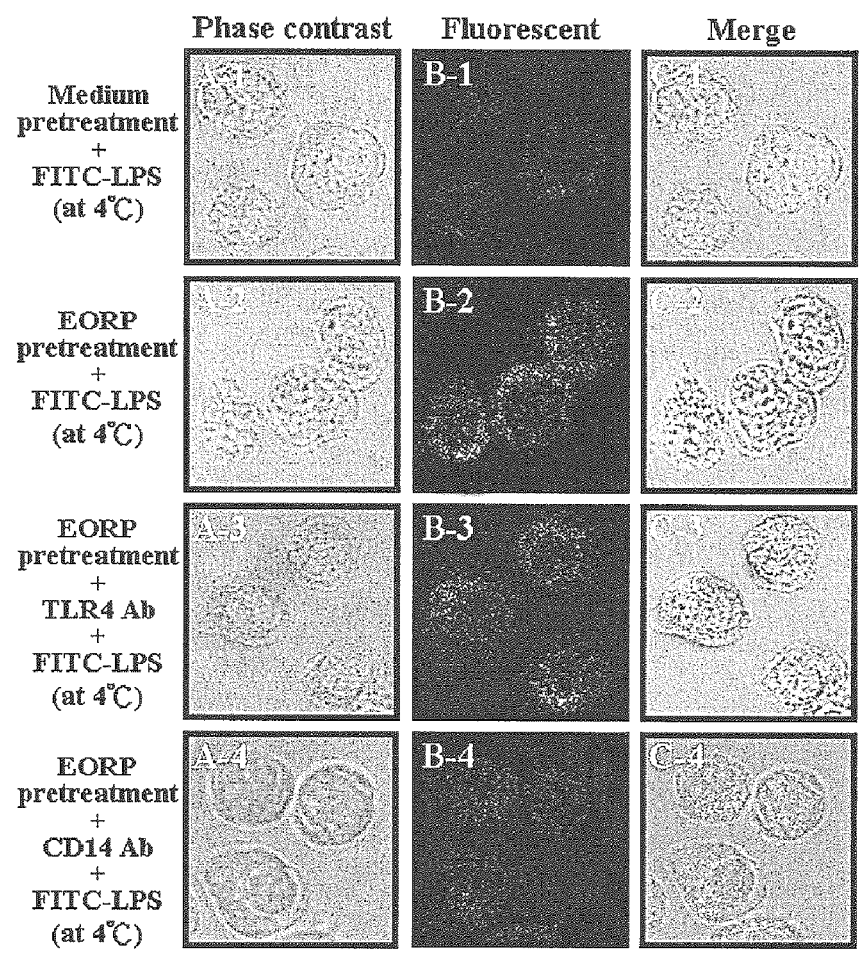
In FIG. 2A, J774A.1 cells were treated with medium or F3 (25 µg/mL) for 24 h followed by fixed with 2% paraformaldehyde. Cells were incubated with control antibody (10 µg/mL), TLR4 blocking antibody (10 µg/mL) or CD14 blocking antibody (10 µg/mL) for 30 min, followed by incubated with FITC-LPS (1 µg/mL) (green) at 4° C. for 30 min, and then examined by confocal microscope.
Figure 2B:
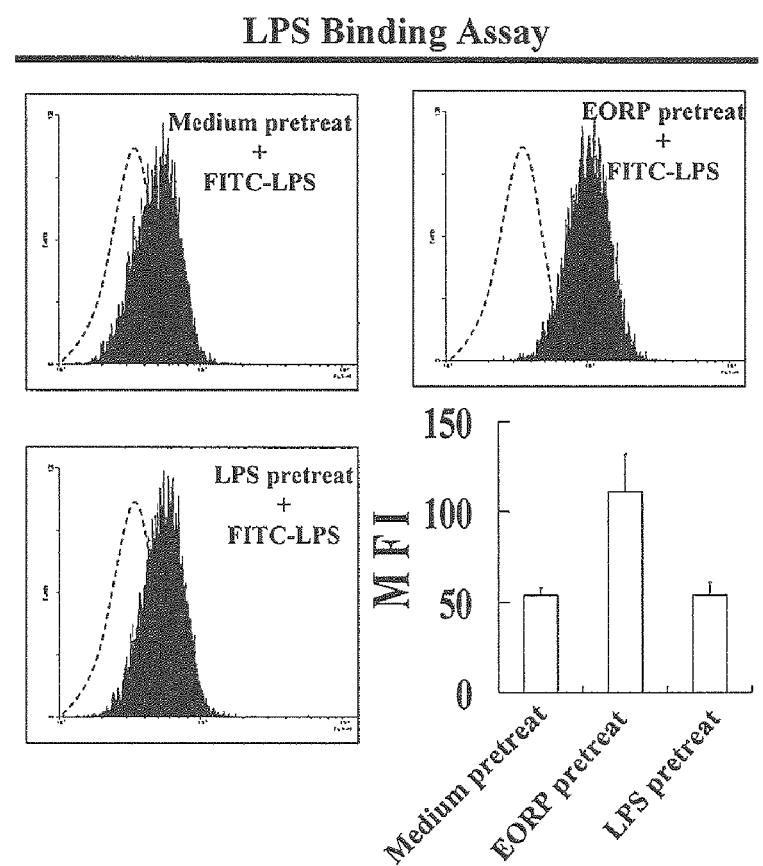
FIG. 2B shows that F3, but not LPS pretreatment increase LPS binding to J774A.1 cells. J774A.1 cells were incubated with medium, F3 (25 g/mL) or LPS (1 µg/mL) for 24 h followed by fixed with 2% paraformaldehyde. Cells were incubated with FITC-LPS (1 µg/mL) at 4° C. for 30 min, and then examined by flow cytometry. Dotted line: no FITC-LPS control; shade: treatment as indicated. The histograms were quantified and represent as mean fluorescence intensity (MFI).

F3 Enhances Macrophage Phagocytosis of LPS Via Increasing LPS Recognition/Binding Affinity and LPS Uptake/Clearance The effects of F3 pretreatment on the recognition/binding and uptake/clearance of LPS by J774A.1 cells was examined. Initially, using confocal microscopy to observe the results of an LPS binding assay, it was found that subsequent to the incubation of FITC-conjugated LPS (FITC-LPS) with fixed J774A.1 cells at 4° C. for a period of 30 min, the amount of cell surface-bound LPS was substantially greater for EORP-pretreated J774A.1 cells (FIG. 2A, panel C-2), than was the case for medium-pretreated J774A.1 cells, i.e., control cells (FIG. 2A, panel C-1). Following this work, the role of TLR4 and of CD14 in LPS recognition/binding by J774A.1 cells was analyzed. As can be seen, pretreatment of J774A.1 cells with CD14 blocking antibody (FIG. 2A, panel C-4), but not with TLR4 blocking antibody (FIG. 2A, panel C-3) prior to FITC-LPS stimulation resulted in significantly reduction of LPS binding to J774A.1 cells surface, indicating that CD14 plays a more important role than TLR4 in LPS binding to J774A.1 cells. In addition, using flow cytometry analysis, it was further confirmed that pretreatment of J774A.1 cells with F3, but not LPS, enhances FITC-LPS binding to the cell surface of J774A.1 cells (FIG. 2B).

Figure 2C:
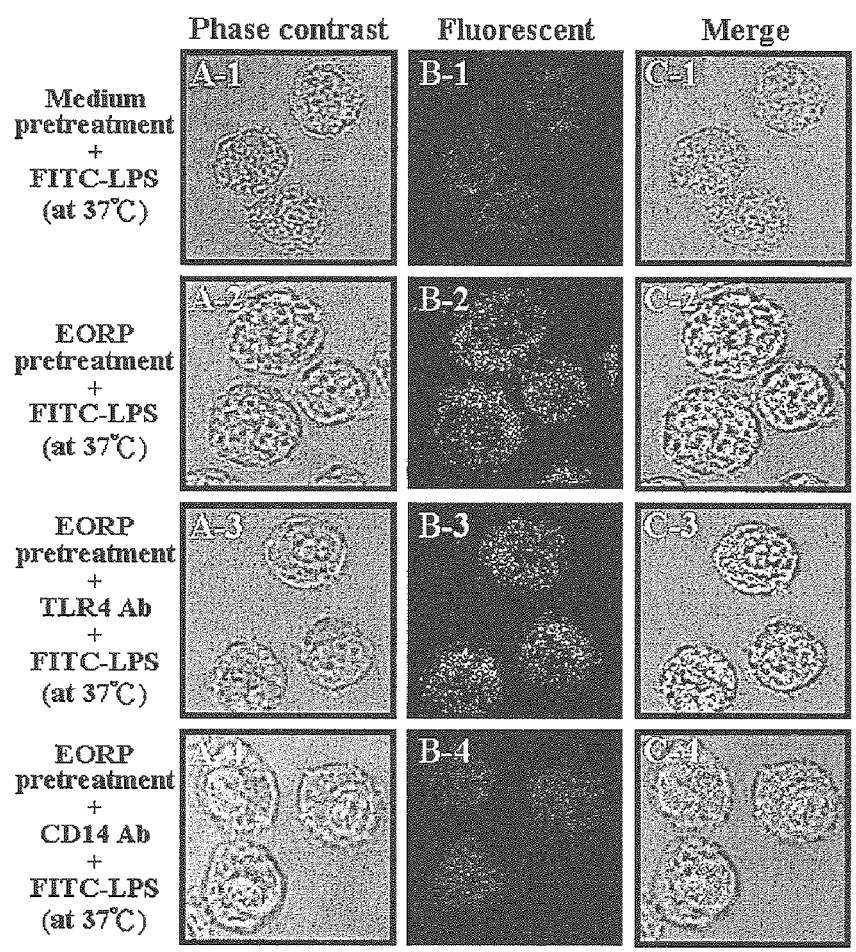
FIG. 2C shows that F3 pretreatment increases LPS internalization by J774A.1 cells. J774A.1 cells were incubated with medium or F3 (25 μg/mL) for 24 h. After washing, cells were incubated with control antibody (10 μg/mL), TLR4 blocking antibody (10 μg/mL) or CD14 blocking antibody (10 μg/mL) for 30 min, followed by incubated with FITC-LPS (1 μg/mL) (green) at 37° C. for 1 h. After fixation and proteinase K (250 μg/mL) treatment, cells were examined by confocal microscope.
Figure 2D:
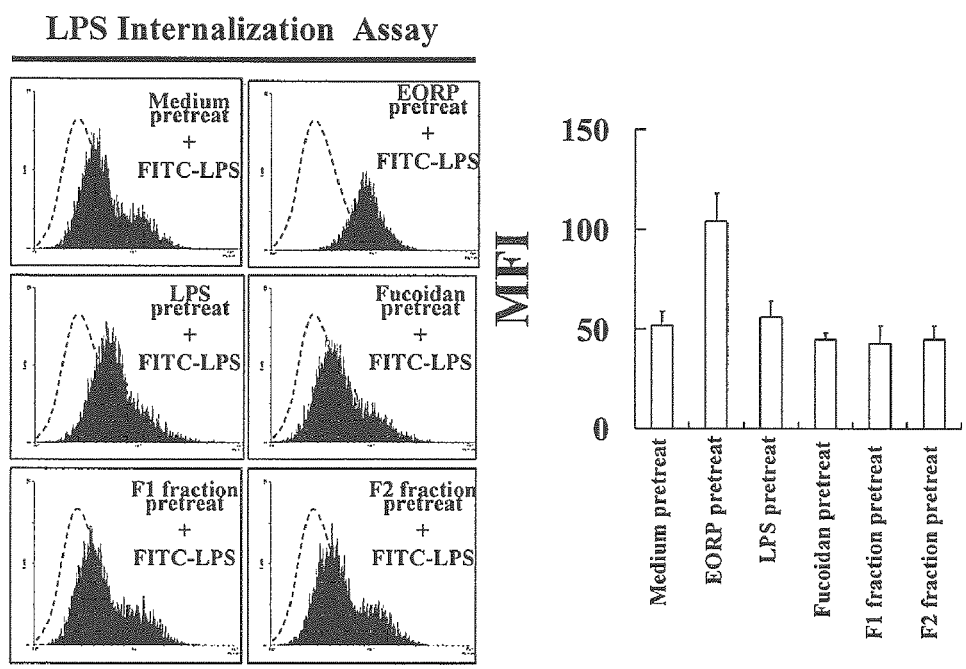
FIG. 2D shows that F3 pretreatment specifically increases LPS internalization by J774A.1 cells. J774A.1 cells were incubated with one of F3 (25 μg/mL), LPS (1 μg/mL), fucoidan (25 μg/mL), F1 fraction of Reishi (25 μg/mL) and F2 fraction of Reishi (25 μg/mL) for 24 h, followed by incubation with FITC-LPS (1 μg/mL) at 37° C. for 1 h. After proteinase K (250 μg/mL) treatment, cells were analyzed by flow cytometry. Dotted line: no FITC-LPS control; shade histograms: treatment as indicated. The histograms were quantified and represent as mean fluorescence intensity (MFI). Note that EORP=F3.

In order to examine the effect of F3 upon LPS uptake/clearance, J774A.1 cells were pretreated with F3 or medium (control), followed by incubation of J774A.1 cells with FITC-LPS at 37° C. for a period of 1 h. Using confocal microscopy to analyse the endocytosis of LPS, it was found that EORP significantly increases J774A.1 cells LPS uptake/clearance (FIG. 2C, panel C-2), compared to analogous cells treated with medium alone (FIG. 2C, panel C-1). In subsequent investigation, it was further demonstrated that the CD14 blocking antibody (FIG. 2C, panel C-4), but not the TLR4 blocking antibody (FIG. 2C, panel C-3) blocks LPS uptake/clearance by J774A.1 cells significantly, indicating that CD14 plays a more-important role than TLR4 in the endocytosis of LPS within J774A.1 cells. Furthermore, using flow-cytometry analysis, it was confirmed that pretreatment of J774A.1 cells with EORP enhances FITC-LPS uptake/clearance by J774A.1 cells; and, in addition, LPS pretreatment enhances FITC-LPS uptake/clearance by J774A.1 cells, although by only a slight amount. Pretreatment of other EORP-related polysaccharide fractions, e.g., F1 and F2, and fucoidan, however, did not increase LPS uptake/clearance, indicating that F3 specifically facilitates macrophages uptake/clearance of LPS (FIG. 2D).

Example 6

Figure 3A:
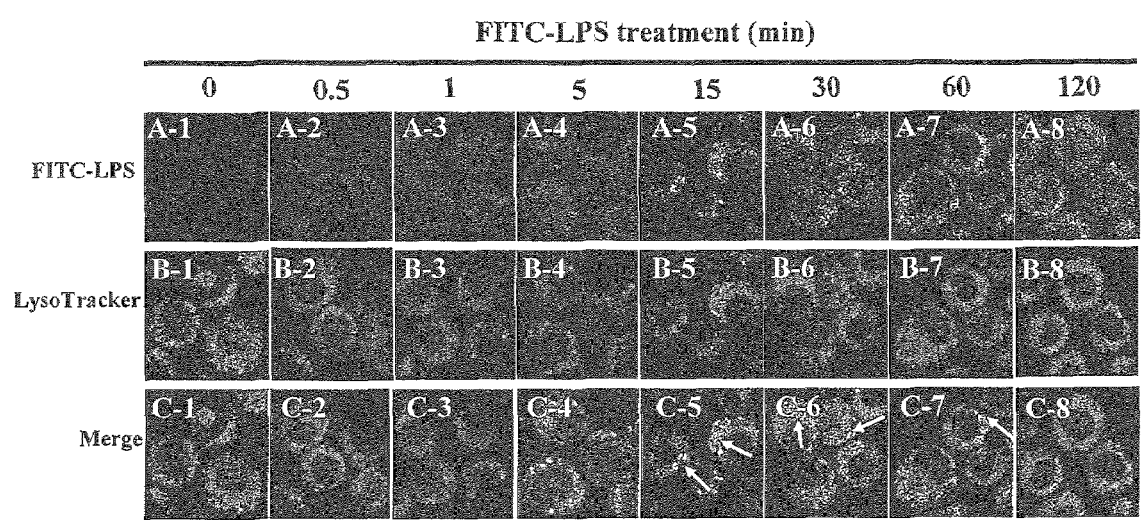
FIG. 3A shows F3-pretreated J774A.1 cells incubated with a lysosome marker (LysoTracker) for 30 min, followed by incubation of FITC-LPS at 37° C. for 0 to 120 min and processed for microscopy.
Figure 3B:
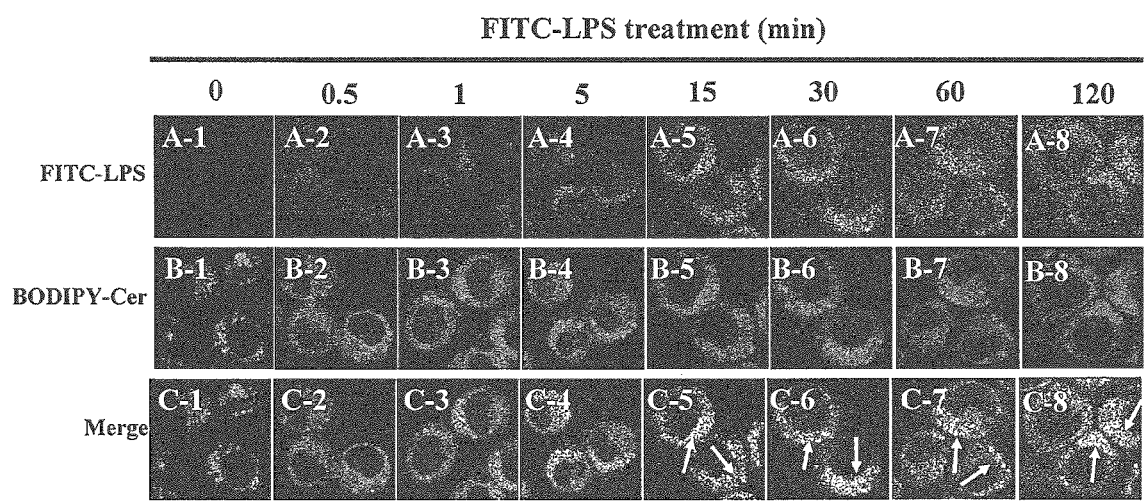
FIG. 3B shows F3-pretreated J774A.1 cells incubated with a Golgi marker (BODIPY-Cer) for 30 min, followed by incubation of FITC-LPS at 37° C. for 0 to 120 min and processed for microscopy. Arrows indicate the merged image of LPS and organelle marker. Note that EORP=F3.

F3 Promotes the Co-Localization of Internalized LPS with *Lysosome* and Golgi Apparatus Markers It has been demonstrated previously that internalized LPS move transiently into an acidic intracellular compartment of human neutrophils [77]. In the current study, in order to examine whether LPS also moves into lysosomes after uptake by F3-pre-treated J774A.1 cells, a fluorescent, freely cell membrane permeable probe, LysoTracker™ Red DND-99 (LysoTracker) was employed. This probe features a high selectivity for acidic organelles [96]. LysoTracker-prelabelled J774A.1 cells were incubated with FITC-LPS at 37° C. for various periods of time, including: 0.5, 1, 5, 15, 30, 60 and 120 min; followed by observation under confocal microscopy whilst cells were still viable. Endocytosis-mediated internalized LPS can be detected as early as 5 min, subsequent to a 15-min period of LPS internalization, and its detection still being possible 120 min subsequent to initial stimulation (FIG. 3A, samples A1-A8). LPS was detected in a perinuclear area of J774A.1 cells and distributed in a tubular pattern after uptake by J774A.1 cells, an observation which is similar to that reported in LPS uptake by murine peritoneal macrophages [97]; yet by contrast, the fluorescent lysosomes were distributed throughout the cytoplasm of J774A.1 cells (FIG. 3A samples B1-B8). The results of merging FITC-LPS and LysoTracker processes revealed that the test cell cellular compartment containing the internalized LPS partially overlapped the lysosomes (FIG. 3A, samples C1-C8). On the other hand, the Golgi apparatus of test J774A.1 cells could be selectively stained with a fluorescent dye BODIPY TR $C_5$-ceramide (BODIPY), which tends to associate preferentially with the trans-Golgi complex [98]. The results of cellular staining assay showed that the punctuate pattern of labelled cells appeared to be similar when stained with either LPS or BODIPY, and that the brightly labelled LPS-containing vesicles colocalized with BODIPY fluorescence during the above-mentioned FITC-LPS uptake assay period of from zero to 120 min at 37° C. (FIG. 3B, samples C1-C8). Comparing the fluorescence intensity in the Golgi apparatus of J774A.1 cells to the fluorescent intensity detected in corresponding lysosomes, there would appear to be a stronger co-localization of LPS and Golgi apparatus, suggesting that more LPS molecules accumulate in the Golgi apparatus of J774A.1 cells after LPS being internalized than congregate within lysosomes. Based upon the current observations showed in FIG. 3, vesicular transport from the plasma membrane of J774A.1 cells appears to deliver LPS to the Golgi apparatus and also to the lysosome, however, other delivery sites for fluorescent-labelled LPS probably also include endosomes and the endoplasmic reticulum of J774A.1 cells after LPS internalization [99].

Example 7

Figure 4A:
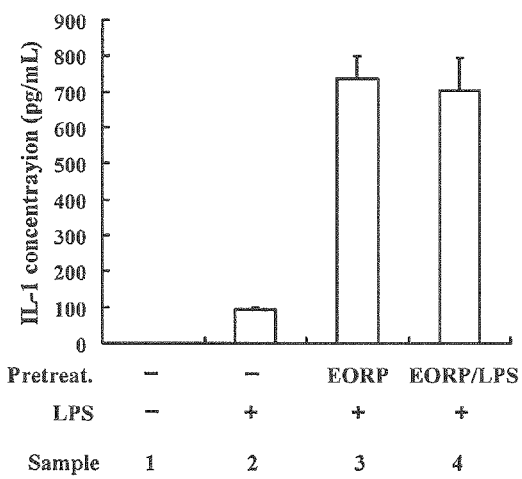
In FIG. 4A, J774A.1 cells (1×10$^6$/mL) were pretreated with F3 (25 μg/mL), F3 (25 μg/mL) plus LPS (1 μg/mL) or medium (control) for 24 h, then challenged with LPS (1 μg/mL) for 24 h. IL-1 concentration in culture supernatant was measured by ELISA. Data shown here expressed as the mean±SD, n=3.
Figure 4B:
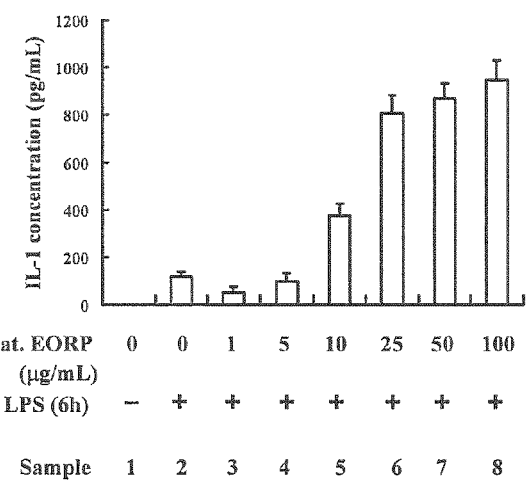
In FIG. 4B, J774A.1 cells (1×10$^6$/mL) were pretreated with the indicated concentration of F3 for 24 h, then challenged with LPS (1 μg/mL) for 24 h. IL-1 concentration in supernatant of cultured cells was measured by ELISA. Data shown here expressed as the mean±SD, n=4.
Figure 4C:
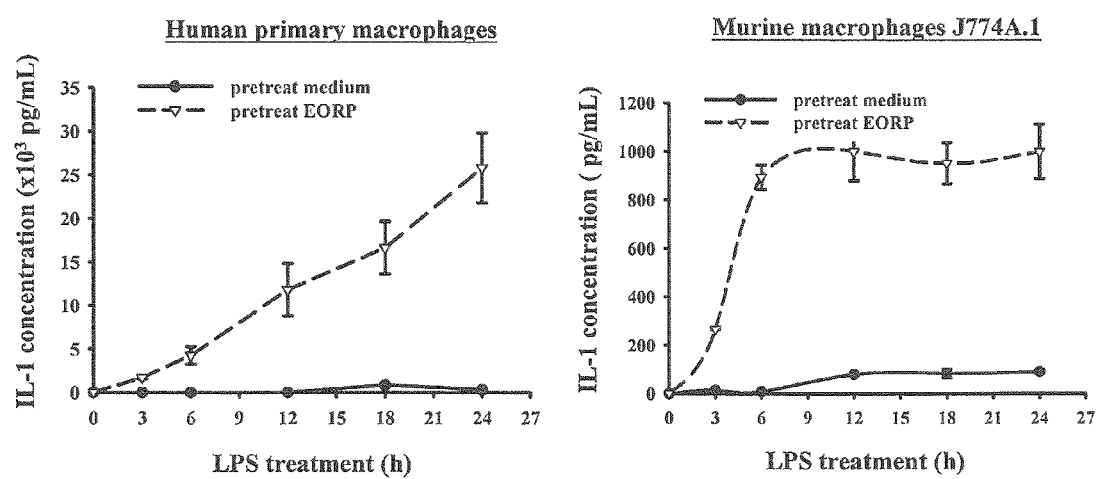
In FIG. 4C, Human blood monocytes-derived macrophages (5×10$^5$/mL) and J774A.1 cells (1×10$^6$/mL) were pretreated with F3 (25 μg/mL) or medium (control) for 24 h, then challenged with LPS (1 μg/mL) for the indicated time points. IL-1 concentration in supernatant of cultured cells was measured by ELISA. Data shown here expressed as the mean±SD, n=4.

F3 Increases IL-1 Secretion within LPS-Stimulated Human Primary Macrophages and within Murine Macrophage J774A.1 Cells Pretreatment of J774A.1 cells with F3 or a mixture of F3 and LPS (F3/LPS) followed by incubation with LPS for a period of 24 h significantly increased IL-1 secretion by J774A.1 cells compared to the case for F3-free controls (FIG. 4A, samples 3 and 4 vs. 1 and 2). From the results of an F3 dose-response study of J774A.1 cells, if the concentration of F3 pretreatment of J774A.1 cells was greater than 25 μg/mL for 24 h, such pretreatment resulted in the LPS-mediated hyperesponsiveness of IL-1 secretion from cells (FIG. 4B). Following such experimentation, it was found that pretreatment of either human primary macrophages or J774A.1 cells (FIG. 4C) with F3 for a period of 24 h substantially increased LPS-induced IL-1 secretion compared to the case for F3-free controls. Moreover, within 24 h of F3 pretreatment, IL-1 secretion into culture supernatant from cultured human macrophages and J774A.1 cells was observed to be, respectively, 25 ng/ml and 1 ng/ml, indicating different reaction kinetics as regards IL-1 secretion apply for human macrophages and murine J774A.1 cells.

Example 8

Figure 4D:
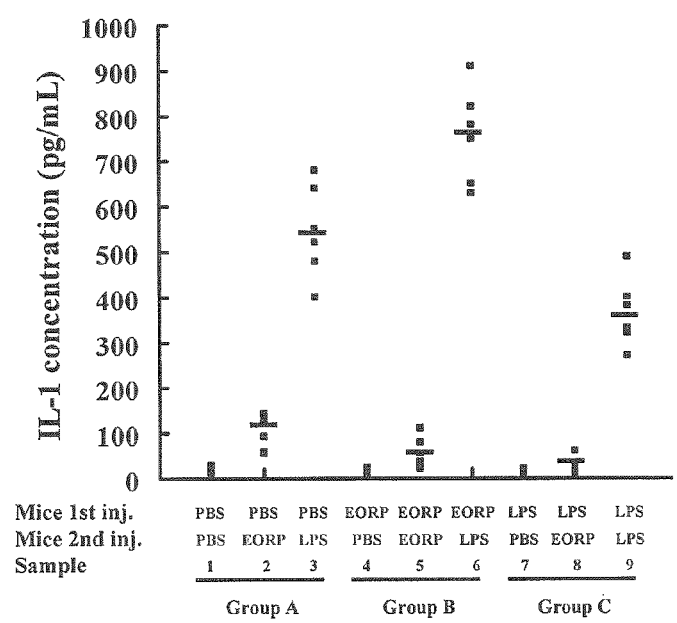
In FIG. 4D, C57BL/6J mice were initially injected intraperitoneally (i.p.) with one of the following, PBS (200 μL), LPS (5 mg/kg) or F3 (100 mg/kg). Twenty-four hours subsequent to such injection, mice were again i.p. with PBS (200 μL), LPS (10 mg/kg) or F3 (200 mg/kg); 1.5 h following which, the concentration of IL-1 in the serum of the tested mice was measured by means of ELISA; n=6.

Preinjection of F3 Increases IL-1 and IL-1Ra Secretion for LPS-Injected Mice In Vivo The in vivo effect of F3 upon LPS-induced cytokine expression in C57BL/6J mice was tested. In brief, C57BL/6J mice were initially injected intraperitoneally (i.p.) with one of the following, PBS, LPS or F3. Twenty-four hours subsequent to such injection, mice were again injected i.p. with PBS, LPS or F3, 1.5 h following which, the concentration of IL-1 in the serum of the tested mice was measured by means of ELISA (FIG. 4D). The mice initially injected i.p. with PBS, F3 or LPS was defined as group A, group B and group C, respectively. Group A mice (FIG. 4D, samples 1-3), revealed that a second LPS injection increased the baseline level of IL-1 secretion by C57BL/6J mice (~550 pg/mL, sample 3) more substantially than was the case for F3 injection (~100 pg/mL, sample 2) or for PBS injection (control) mice (basal level, sample 1). For group B, mice were initially i.p. injected with F3 for 24 h, followed by a second injection with one of PBS, F3 or LPS for 1.5 h (samples 4-6, respectively). The results of such treatments indicated that F3 significantly increased LPS injection-induced IL-1 secretion from mice (~800 pg/mL, sample 6), such increase in IL-1 secretion not being the case for mice injected with either F3 (~50 pg/mL, sample 5) or PBS (basal level, sample 4) as the second injection. For group C, mice were initially i.p. with LPS for a period of 24 h, followed by again injection with one of PBS, F3 or LPS (samples 7-9, respectively). A second injection of LPS induces lower IL-1 secretion in mice serum (~400 pg/mL, sample 9) compared to the case for single LPS injected mice (group A, sample 3). By contrast, F3 and PBS injection did not induce significantly IL-1 secretion in mice serum (samples 6 and 7).

Although F3 was observed to largely increase LPS-induced IL-1 expression by C57BL/6J mice (FIG. 4D, group B, sample 6), it did not increase the relative toxicity of LPS in the tested mice evidenced as injury or death (data not shown), thus F3 was able to stimulate some sort of "protection" factor(s) from mice. The possibility that F3 increases the level of IL-1 receptor antagonist (IL-1Ra) expression was investigated. As can be seen from FIG. 4E, there appears to be no evidence of the presence of IL-1Ra in the serum of PBS-injected mice or control mice (data not shown). By contrast, however, at 3 h post-F3 injection of test mice, IL-1Ra concentration in mice serum was substantially induced by the injection of F3, the level of IL-1Ra reaching to around 5,000 pg/mL (sample 2) in mice serum three hours subsequent to F3 injection, although it was also observed that LPS injection into C57BL/6J mice increased IL-1Ra concentration (~2,000 pg/mL) in serum.

Figure 4E:
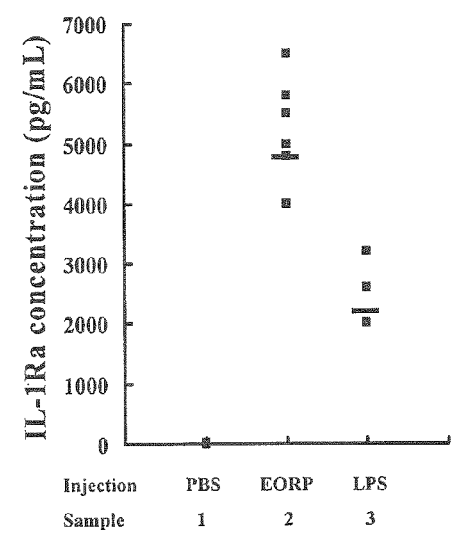
In FIG. 4E, C57BL/6J mice were i.p. with one of the following, PBS (200 μL), LPS (10 mg/kg) or F3 (200 mg/kg), 3 h following which, the concentration of IL-1Ra in the serum of the tested mice was measured by ELISA. Data shown here expressed as the mean±SD, n=6.
Figure 4F:
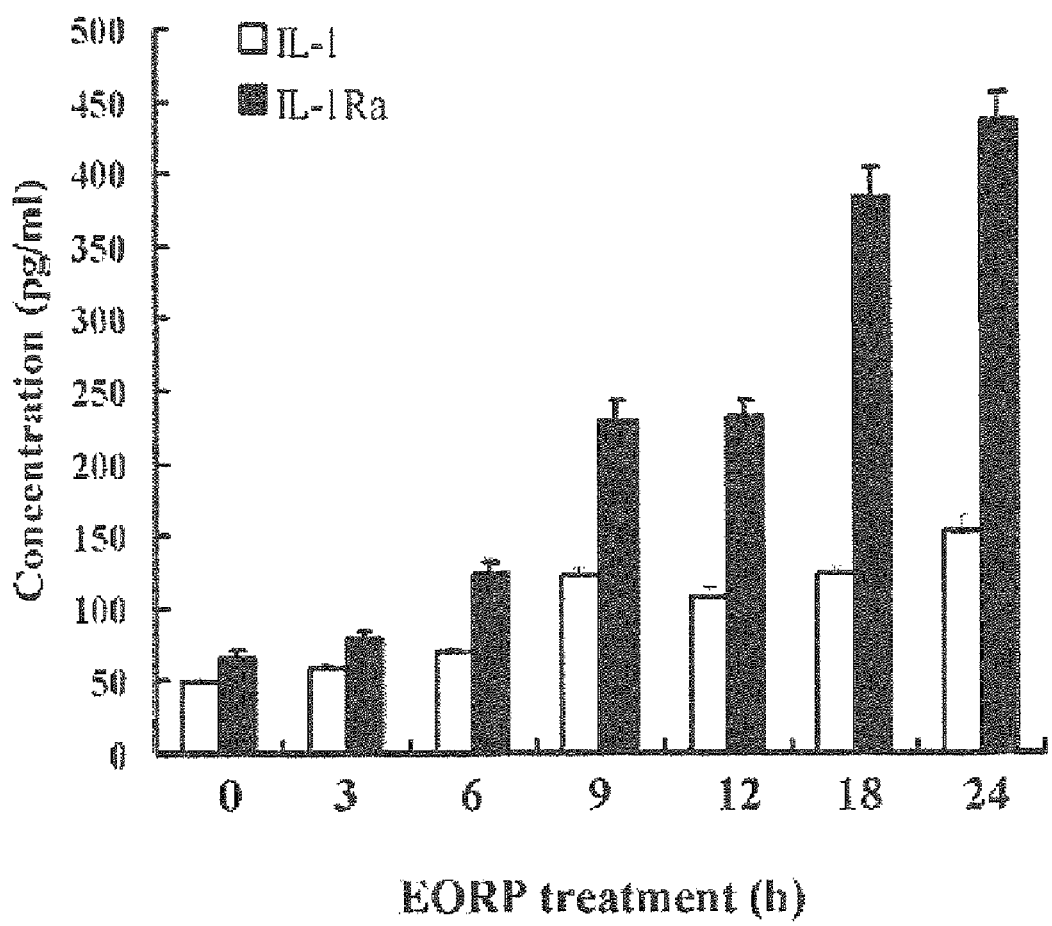
FIG. 4F shows that F3 induces IL-1Ra and IL-1 secretion, respectively within human THP-1 monocytes. Human THP-1 monocytes (1×10$^6$/mL) were treated with F3 (100 μg/mL) during a testing period of from zero to 24 h. The concentrations of released IL-1Ra and IL-1, respectively in conditioned media are measured by ELISA technique, data shown here expressed as the mean±SD, n=4. Note that EORP=F3.

The effect of F3 on IL-1Ra and IL-1 secretion within human THP-1 monocytes was also investigated. Monocytes were treated with F3 during a testing period of from zero to 24 h, the concentrations of released IL-1Ra and IL-1, respectively in conditioned media are measured by ELISA. As shown in FIG. 4F, F3 substantially increases more secretion of IL-1Ra than of IL-1 by 2 to 4 folds within 12 to 24 h, respectively post-stimulation of human THP-1 monocytes. In addition, F3 treatment also increases IL-1Ra secretion from cultured murine macrophages J774A.1 cells and human primary macrophages.

Example 9

Figure 5A:
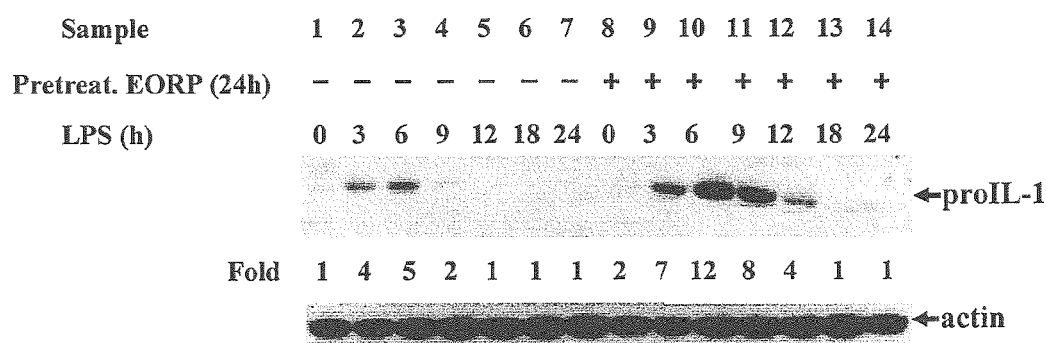
In FIG. 5A, J774A.1 cells were pretreated with F3 (25 μg/mL) or medium for 24 h, then challenged with LPS (1 μg/mL) for the indicated time points. ProIL-1 protein production was analyzed by Western-blotting; n=3.
Figure 5B:
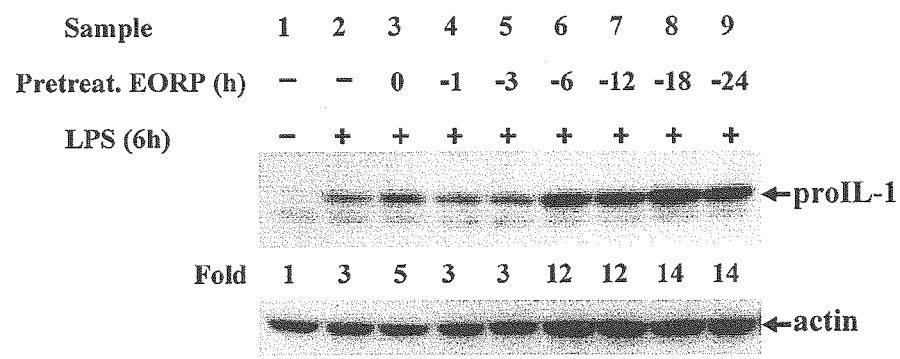
In FIG. 5B, J774A.1 cell were pretreated with F3 for the indicated time points prior to LPS stimulation for 6 h. ProIL-1 protein production was analyzed by Western-blotting. n=4.
Figure 5C:
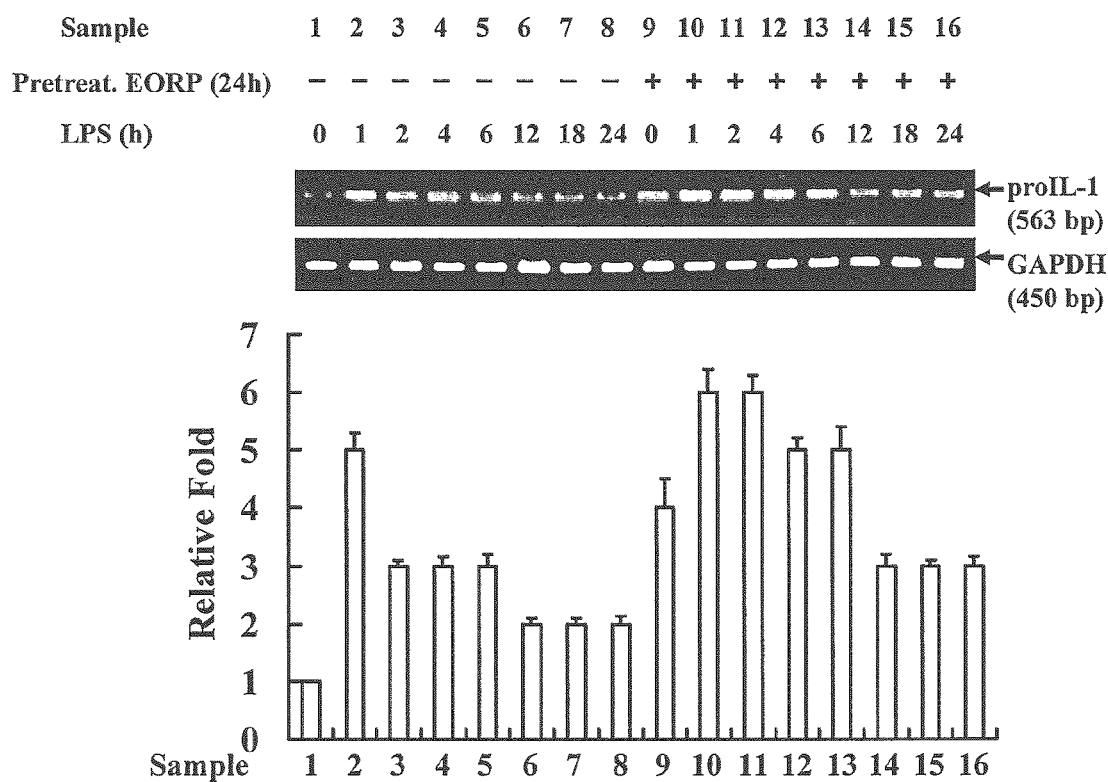
In FIG. 5C, J774A.1 cells were pretreated with F3 (25 μg/mL) or medium for 24 h, and then stimulated with LPS (1 μg/mL) for the indicated time points. IL-1 and GAPDH mRNA expression level were analyzed by RT-PCR. n=3. Note that EORP=F3.

Mechanism by which F3 Pretreatment of Macrophages Increases LPS-Induced Pro-IL-1/IL-1 Expression In order to investigate the mechanism of F3 boosting LPS-induced IL-1 secretion by J774A.1 cells, the effect of F3 pretreatment upon proIL-1 protein production by J774A.1 cells subjected to subsequent LPS stimulation was investigated. Prointerleukin-1 (proIL-1, 34 kD), an IL-1 precursor is translated from IL-1 mRNA and cleaved into a mature secreted form of IL-1 (17 kD) by interleukin 1-converting enzyme (ICE) [85]. The production of proIL-1 protein within J774A.1 cells was investigated using Western-blotting analysis. Using a time-course study, proIL-1 production was detected in cell lysate between three and nine hours subsequent to LPS stimulation, the proIL-1 protein level peaking at 6 h, and the proIL-1 protein level in cell lysate gradually returning to the basal level at around 12 h subsequent to LPS stimulation (FIG. 5A). By contrast, for J774A.1 cells pretreated with F3, followed by LPS stimulation, the level of proIL-1 protein expression was greater for such pretreated cells than was the case for un-pretreated J774A.1 cells (FIG. 5A). Following such investigation, the necessary F3 incubation time for cultured J774A.1 cells so as to allow them to develop the "hyper-induction" of proIL-1 protein expression was determined. In brief, during a 24 h period, at various specific times (i.e. commencement, 1, 3, 6, 12, 18, and 24 h subsequent to F3 pretreatment), such F3 pretreatment of J774A.1 cells was halted by washing with PBS, followed by LPS challenge for an additional six hours. Following this, Western-blotting analysis of proIL-1 production indicated that a minimum pretreatment of J774A.1 cells with F3 for a period of around three to six hours was required to induce "hyper-induction" of proIL-1 protein expression (FIG. 5B). Furthermore, in order to investigate whether F3 modulates LPS-induced IL-1 gene expression at the transcriptional level, the IL-1 mRNA expression level was analysed by RT-PCR method. It was found that LPS-induced IL-1 mRNA expression for F3-pretreated J774A.1 cells were greater than was the case for un-pretreated counterpart cells (FIG. 5C). A similar result for IL-1 mRNA expression was also observed using Northern blotting assay.

Example 10

F3 Pretreatment Up-Regulates LPS-Induced proIL-1/IL-1 Expression Via Activation of Mitogen Activated Protein Kinases (MAPKs)

Figure 6A:
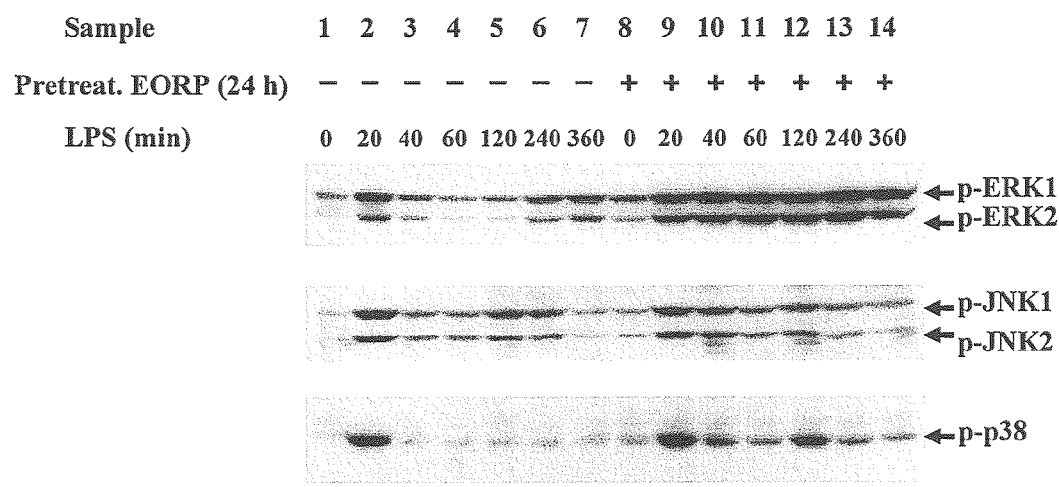
In FIG. 6A, F3 pretreatment up-regulates LPS-induced MAPKs phosphorylation. J774A.1 cells were pretreated for 24 h with F3 (25 μg/mL) or medium and challenged with LPS (1 μg/mL) for the indicated time points. Phosphorylation level of ERK, JNK, and p38 were analyzed by Western-blotting with anti-diphosphorylated ERK, anti-diphosphorylated JNK or anti-diphosphorylated p38 monoclonal antibody, respectively. One of three experiments is presented.

In order to further investigate the effect of F3 upon LPS-mediated signaling related to IL-1 gene expression, the effect of F3 pretreatment of J774A.1 cells on the LPS-mediated downstream activation of MAPKs was investigated. It was found that LPS rapidly induced the activation of ERK, JNK, and p38 (FIG. 6A, samples 1-7); whereas, by contrast, pre-exposure of J774A.1 cells to F3 resulted in the rapid and substantial enhancement of the LPS-mediated activation of ERK, JNK, and p38 (FIG. 6A, samples 8-14). More specifically, in the first instance, the phosphorylation level of ERK reached a peak at around 20 min subsequent to LPS stimulation, and returned to the basal level at around 60 min subsequent to LPS stimulation. Further, the phosphorylation level of ERK was increased again at 240 and 360 min subsequent to LPS stimulation. Interestingly, for F3-pretreated J774A.1 cells, the phosphorylation level of ERK proved to be, 1.5, 3, 6, 5, 2.5, and 1.5-fold greater than corresponding values for F3-free cells at, respectively, 20, 40, 60, 120, 240, and 360 min subsequent to LPS stimulation (FIG. 6A). The presence of phosphorylated JNK at a significant level above baseline was detected at around 20 min subsequent to LPS stimulation, whereas the level of LPS-induced JNK phosphorylation increased to only a slight extent for the F3-pretreated J774A.1 cells (FIG. 6A). The phosphorylation level of p38 quickly reached the maximal level at around 20 min subsequent to LPS stimulation, the level reducing significantly 40 min subsequent to LPS stimulation, although p38 phosphorylation again began to rise at around 240~360 min subsequent to LPS stimulation. For F3-pretreated J774A.1 cells, the phosphorylation level of p38 following LPS stimulation was, 1, 4, 2, 3, and two-fold greater than the corresponding level for un-pretreated J774A.1 cells at, respectively, 20, 40, 60, 120, and 240 min subsequent to LPS stimulation (FIG. 6A).

Figure 6B:
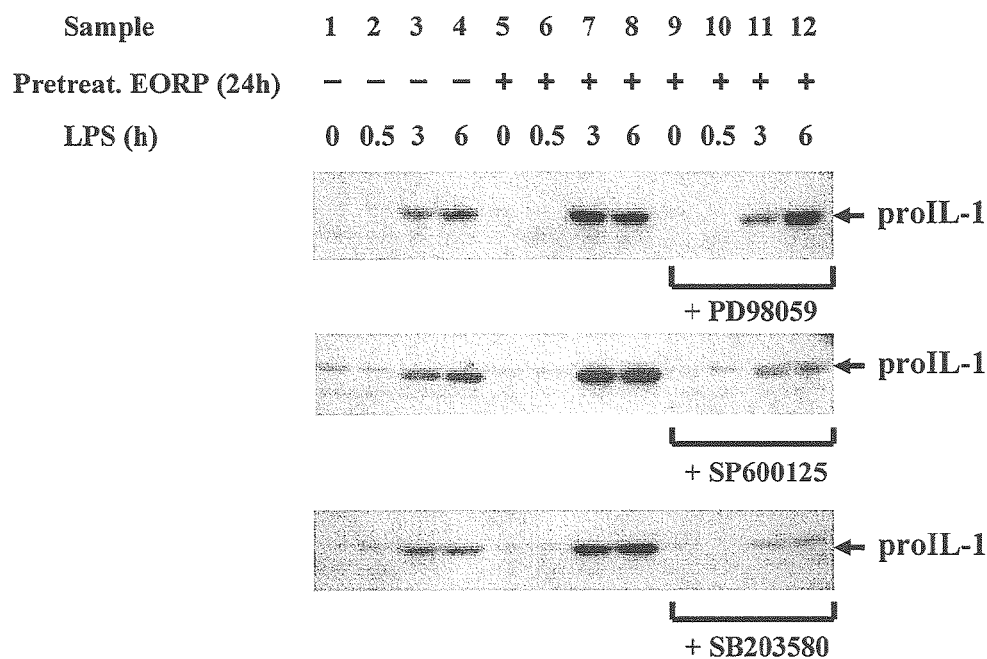
In FIG. 6B, J774A.1 cells were pretreated for 24 h with F3 (25 μg/mL) or medium and stimulated with LPS (1 μg/mL) for the indicated time points in the present or absence of protein kinase inhibitors as indicated. ProIL-1 protein expression level was analyzed by Western-blotting. One of three experiments is presented. Note that EORP=F3.

Three pharmacological protein kinase (PK) inhibitors were used to further assess the correlation between the F3-enhanced activation of the studied MAPKs and the corresponding cytokine expression. Following F3 pretreatment and prior to LPS treatment, J774A.1 cells were incubated with one of PD98059, SP600125 or SB203580, agents which specifically inhibit the activity of, respectively, MEK1, JNK, and p38. The dose-response performance for the specific PK inhibitors tested was monitored by directly assaying individual PK activity [93]. As can be seen from FIG. 6B, application of the JNK inhibitor (SP600125) and the p38 inhibitor (SB203580) significantly blocked F3 enhancement of LPS-induced proIL-1 protein expression. The application of PD98059 (a MEK inhibitor), however, did not appear to diminish LPS-induced proIL-1 protein expression for F3-pretreated J774A.1 cells (FIG. 6B), indicating that the pathway of MEK→ERK plays a less-significant role than JNK and p38 related pathways as regards the induction of proIL-1. Furthermore, as measured by application of an MTT assay, no evidence of a cytotoxic effect was observed subsequent to J774A.1 cells treatment with any of the PK inhibitors, at the specific concentrations at which these inhibitors were used (data not shown). Taken together, these results indicate that F3 pretreatment of cultured J774A.1 cells up-regulates LPS recognition and clearance by J774A.1 cells as well as the activation of certain MAPKs, leading to proIl-1/IL-1 expression.

Example 11

Effect of LPS Uptake/Internalization Upon LPS-Mediated Activation and Signalling Related to IL-1 Gene Expression Cultured J774A.1 cells were preincubated with F3 in the presence or absence, individually, of the endocytosis inhibitors cytochalasin D [100] and colchicine [101], and the effect of such endocytosis inhibitors upon F3-induced LPS uptake/internalization was studied. As can be seen from confocal microscopy investigation (FIG. 7A), the presence of cytochalasin D (sample C-3) and also that of colchicine (sample C-4) significantly blocked the internalization of FITC-LPS compared with the analogous results for cytochalasin D/colchicine-free cells (FIG. 7A, samples C-2).

Figure 7B:
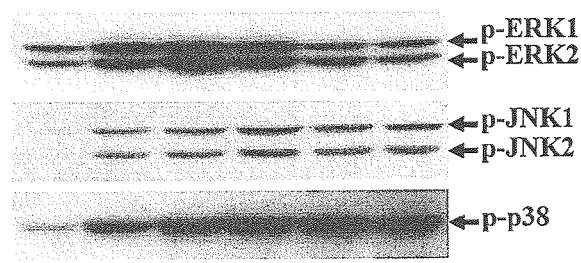
In FIG. 7B, the effect of endocytosis inhibitors on LPS-induced MAPKs phosphorylation in J774A.1 cells is shown. J774A.1 cells were pretreated for 30 min with cytochalasin D (1 and 10 μM) or colchicine (10 and 30 μM) before being exposed to LPS (1 μg/mL) for 15 min. Phosphorylation level of ERK, JNK, and p38 were analyzed by Western-blotting with anti-diphosphorylated ERK, anti-diphosphorylated JNK or anti-diphosphorylated p38 monoclonal antibody, respectively. One of three experiments is presented.

The LPS-induced downstream activation of test MAPKs and also IL-1 gene expression by J774A.1 cells was examined in the presence, separately, of the endocytosis inhibitors, cytochalasin D and colchicine. Binding of LPS to J774A.1 cells was observed to quickly induce phosphorylation of the MAPKs (ERK, JNK, and p38) (FIG. 7B, sample 2).

Figure 7C:
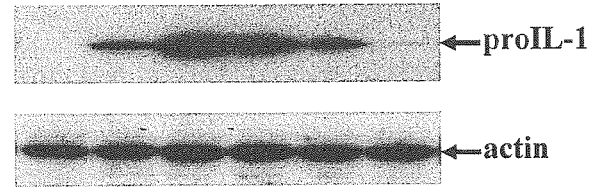
In FIG. 7C, the effect of endocytosis inhibitors on LPS-induced proIL-1 production within J774A.1 cells is shown. J774A.1 cells were pretreated with cytochalasin D (1 and 10 μM) or colchicine (10 and 30 μM) for 30 min, followed by LPS treatment for 6 h, and then whole cell lysates were analyzed for proIL-1 protein by Western-blotting. One of three experiments is presented.

Although endocytosis inhibitors such as cytochalasin D and colchicine both exerted profound inhibitory effects upon LPS uptake/internalization (FIG. 7A, samples C-3 and C-4), their effects upon J774A.1 cells activation and signaling would appear to be quite different. For example, both cytochalasin D and colchicine enhance p38 phosphorylation, and cytochalasin D up-regulates the phosphorylation level of ERK1/2, whereas colchicine acts to the contrary, it diminishing the phosphorylation level of ERK1/2 (FIG. 7B). When comparing such activity with LPS treatment of cultured J774A.1 cells, cytochalasin D "super"-induces LPS-mediated proIL-1 production, whereas, by contrast, colchicine exerts a significantly lower impact upon proIL-1 induction. Further, at a relatively substantial concentration (30 μM), colchicine actually inhibits proIL-1 production (FIG. 7C).

Figure 7D:
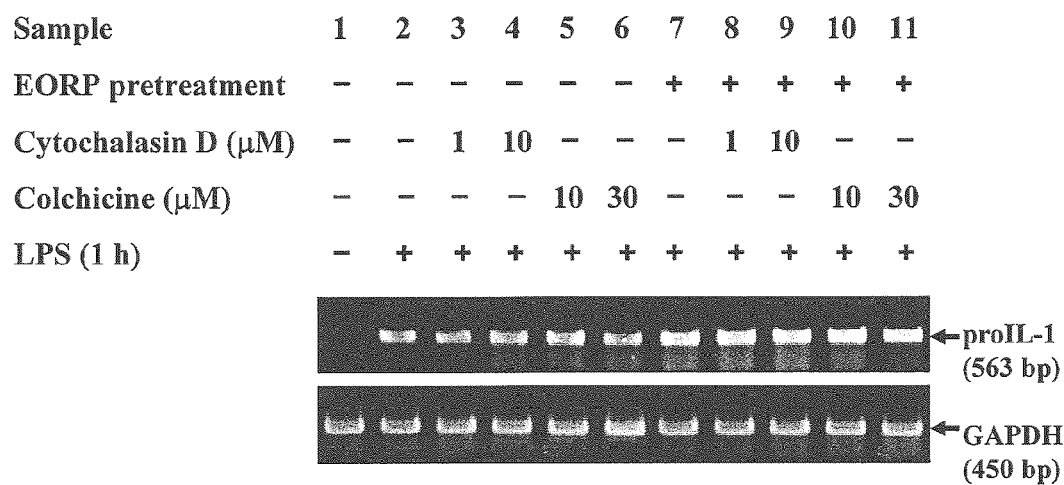
In FIG. 7D, the effect of endocytosis inhibitors on LPS-induced IL-1 mRNA expression within J774A.1 cells is shown. J774A.1 cells were pretreated for 30 min with cytochalasin D (1 and 10 μM) or colchicine (10 and 30 μM) before being exposed to LPS (1 μg/mL) for 1 h. IL-1 mRNA expression were analyzed by RT-PCR. One of three experiments is presented. Note that EORP=F3.

Using RT-PCR method, the effect of cytochalasin D and colchicine upon IL-1 mRNA expression was examined. As can be seen from FIG. 7D, there would not appear to be any significant difference in IL-1 mRNA expression between the treatment of cultured J774A.1 cells with cytochalasin D, colchicine or LPS, either with or without F3 pretreatment (FIG. 7D). At reasonably large doses, colchicine inhibited proIL-1 protein production but did not affect IL-1 mRNA expression, suggesting that colchicine interferes with IL-1 mRNA translation. Importantly, no cytotoxic effect of cytochalasin D and colchicine upon cultured J774A.1 cells was observed as measured by an MTT assay (data not shown) during which assay, these cells were treated with various doses of cytochalasin D or colchicine, the results indicating that colchicine inhibition of proIL-1 production within J774A.1 cells was unlikely to be due simply to cell damage.

The results of Examples 4-11 demonstrate that a fucose containing glycoprotein fraction of *Ganoderma lucidum* polysaccharides (EORP/F3) can modulate the immune response of macrophages by enhancing CD14-mediated endocytosis and by increasing TLR4-regulated IL-1 gene expression. In essence, the Examples demonstrate that F3 increased the surface expression of both CD14 and TLR4, and promoted macrophage-mediated phagocytosis of LPS. Moreover, F3 pretreatment increased the level of LPS-induced IL-1 secretion in mice in vivo as well as within cultured human blood-derived primary macrophages, and murine J774A.1 macrophages in vitro. In addition, the serum concentration of IL-1Ra was dramatically increased for mice undergoing F3 injection, as compared to the basal level of IL-1Ra release as revealed by analogous PBS injection. It has been demonstrated here for the first time that CD14-mediated LPS endocytosis and TLR4-regulated IL-1 gene expression within macrophages are two separate and independent events.

The cellular uptake/clearance of certain bacteria and bacterial components (e.g., LPS) is predominantly performed by phagocytosis conducted by macrophages. Phagocytosis by macrophages is one of the most-important features of the innate anti-bacterial immune response, and requires the specific recognition of certain bacteria or bacterial components and endocytic pathways [102]. The clearance of LPS is a critical step for these cells' defence mechanism and one that reduces the relative toxicity of LPS, whilst still preserving some of these agents' potentially beneficial inflammation-related immune response-riggering stimuli [77]. LPS is able to be recognized by various macrophage-cell surface molecules such as TLR4, CD14 [103] and MSR [88]. The foregoing examples demonstrate that LPS decreased TLR4 surface expression for cultured J774A.1 macrophages; but increased the cell-surface expression of MSR, an outcome which could explain the reason for the observation herein that LPS pretreatment did increase LPS uptake by cultured macrophages, albeit only slightly; whereas, by contrast, F3 down-regulated the surface expression of MSR, but significantly up-regulated the surface expression of both TLR4 and CD14. Moreover, only F3, but not the related fractions of *G. lucidum* polysaccharides, F1 and F2, increased LPS binding to J774A.1 cells and uptake by J774A.1 cells.

Using the TLR4 and CD14 blocking antibodies, which block TLR4 and CD14 binding to their ligands, the foregoing examples have demonstrated that CD14 is crucial for LPS binding to J774A.1 cells and uptake by J774A.1 cells, although surface expression of TLR4 does not correlate well with the level of such LPS binding to J774A.1 cells. Such an outcome suggests that in the presence of LPS, TLR4 is only involved with LPS-mediated signaling but has nothing to do with LPS binding and uptake by J774A.1 cells, a result which would appear to be entirely consistent with the results of certain other related studies [78].

Although CD14 plays an important role in the process of LPS binding and uptake by J774A.1 cells, the presence of CD14 blocking antibody in culture does not completely inhibit F3-enhanced LPS binding and uptake by J774A.1 cells, suggesting that certain additional mechanism(s) are involved in this specific process.

In addition to the activation of J774A.1 cells, the foregoing examples show that membrane-bound CD14 plays another important role in endocytosis, a role that requires cytoskeleton rearrangements and polymerization [78-79]. The foregoing examples show that both cytochalasin D (blocking actin polymerization [100]) and colchicine (blocking microtubule polymerization [101]) significantly reduced the level of endocytosis of FITC-LPS; but elicited no interference with LPS-induced IL-1 mRNA expression, indicating that the two processes, endocytosis and signal transduction, are normally independent. In addition, the foregoing examples revealed that cytochalasin D increased the level of LPS-induced proIL-1 production, as well as increasing the level of ERK, JNK, and p38 activation. Cytochalasin D disruption of actin polymerization may therefore prompt one certain type of stress for J774A.1 cells, and this stress may intervene in the downstream propagation of mitogenic and/or activation signals [104]. By contrast, the foregoing examples demonstrate that colchicine selectively enhanced LPS-induced p38 activation, but diminished proIL-1 production at a high concentration, suggesting that colchicine inhibits certain proIL-1/IL-1 protein translation processes [105].

The foregoing examples show that the acquired hyper-responsiveness of IL-1 gene expression via F3 is characterized by the increased ability of LPS to stimulate steady-state levels of IL-1 mRNA, proIL-1 protein, IL-1 secretion, and MAPK activation, but not the ICE activity level (data not shown) within cultured J774A.1 cells. Furthermore, the foregoing examples demonstate that such LPS stimulation also encompasses the enhancement of the serum level of IL-1 secretion, in vivo, for mice that have been i.p. injected with LPS. The increasing level of F3-mediated up-regulation of IL-1 secretion by J774A.1 cells was observed to be more substantial than the corresponding level increase of the proIL-1 protein production. By contrast, F3 pretreatment decreases LPS-induced TNF secretion (data not shown).

The foregoing examples demonstrate that pre-exposure of J77A.1 cells to F3 dramatically increases the LPS induction of ERK, JNK and p38 activation. By contrast, however, LPS pretreatment of J774A.1 macrophages appears to induce a state of cellular hyporesponsiveness to subsequent challenge with LPS, leading to a significant suppression of ERK, JNK and p38 activation within certain macrophages, such an outcome being termed LPS tolerance [106-108].

Using inhibitors of the activation of certain protein kinases, the foregoing examples have demonstrated that SP600125 (JNK inhibitor) and SB203580 (p38 inhibitor), but not PD98059 (MEK1 inhibitor), inhibit the F3-mediated upregulation of proIL-1 protein production, indicating that F3 upregulation of proIL-1 protein results, principally, from the enhanced activation of JNK and p38. Moreover, the foregoing examples demonstrate that F3 stimulation of cultured J774A.1 macrophages led to a rapid degradation of IRAK-1 protein in cytosol and the slight down-regulation of the expression of IRAK-2 and IRAK-M (data not shown). Furthermore, such F3 stimulation also led to the retention of a similar steady-state level of the protein MyD88 (data not shown). Since IRAK-M has been reported to be an important negative regulator of LPS-mediated signal transduction related to cytokines expression [109], the results appear to suggest that the F3-mediated enhancement of IL-1 gene expression followed by LPS challenge is probably, at least partially, due to the associated reduction in IRAK-M expression by F3 treatment.

It has been reported previously that the administration of IL-1 protected mice from lethal E-coli infection as compared to untreated mice [87]. Herein, the foregoing examples have demonstrated that F3 pretreatment enhances LPS-induced IL-1 secretion by mice, as well as enhancing LPS-induced IL-1 secretion by cultured human primary macrophages, and J774A.1 macrophages in vitro, a scenario which may provide some form of protection effect for host species in response to pathogen challenge. Although F3 was observed to increase LPS-induced IL-1 expression, interestingly, F3 also dramatically enhanced interleukin-1 receptor antagonist (IL-1Ra) secretion by C57BL/6J mice within 3 h intraperitoneal injection of LPS (FIG. 4E). Since IL-1Ra is a member of the IL-1 superfamily, the actions of which include the competitive inhibition of the binding of IL-1 to an IL-1 receptor (IL-1R) [90], the current "parallel" F3 regulation of IL-1 and IL-1Ra within human THP-1 monocytes (FIG. 4F) could, in fact, be part of a protective mechanism designed to preserve the level of access of IL-1 to IL-1R [110]. The increase in the serum level of IL-1Ra for F3-treated mice and cultured macrophages would appear to reduce the availability of the IL-1 to IL-1R; therefore, the net reaction may be to shift the biological functions of IL-1 back toward baseline. The current results suggest that the concentration of IL-1Ra in serum and conditioned medium deriving from, respectively, F3-stimulated mice and macrophages, was substantially larger than corresponding levels for controls, such an outcome likely leading to an increase of serum and supernatant of cultured cells in the level of soluble IL-1 (non-receptor bound IL-1) during LPS stimulation.

Taken together, Example 23-30 demonstrate that F3 enhances the innate immunity related phagocytosis ability of macrophages, by increasing surface expression of CD14 and TLR4, respectively, as well as by enhancing CD14-dependent binding and endocytosis of LPS for cultured macrophages. F3 also promotes the TLR4-mediated hyper-responsiveness of IL-1 gene expression and the activation of MAPKs for cultured macrophages subsequent to LPS challenge. In addition, F3 challenge dramatically increases IL-1Ra expression by mice and by human monocytes. The results of endocytosis-inhibitor blockade of LPS internalization in the absence of any apparent interference with LPS-dependent activation for J774A.1 macrophages indicate that these two outcomes (endocytosis/phagocytosis and signal transduction) are independent. The ability of the fucose-containing glycoprotein fraction from *Ganoderma lucidum* to enhance these components of the innate immunity system that are important for the body's response to LPS challenge indicates that the fucose-containing glycoprotein fraction will be useful for the treatment of bacterial infections, and for the prevention of bacterial infections.

Example 12

Experimental Methods and Materials

The following materials and methods were used in Examples 4-11.

Cell Cultures

Using Histopaque®-1077 method, human blood monocytes-derived macrophages were isolated from blood of healthy persons obtained from Taiwan Blood Center (Taipei, Taiwan). J774A.1 cells were obtained from ATCC (Rockville, Md.). All cell cultures were propagated in RPMI 1640 medium supplemented with 10% heated-inactivated fetal bovine serum and 2 mM L-glutamine and cultured in a 37° C., 5% $CO_2$ incubator.

Study of IL-1 Production Challenged with LPS and EORP in Mice Model

Pyrogen-free male C57BL/6J mice (8- to 10-week old and averaged 18~22 g) were purchased from National Laboratory Animal Center (Taipei, Taiwan). All animal procedures were conducted under a license from the Institutional Animal Care and Use Committee at the National Yang-Ming University. Mice were intra-peritoneal injected of 100 mg/kg EORP, 5 mg/kg LPS or an equal volume of PBS (200 µL) 24 h before LPS (10 mg/kg) or EORP (200 mg/kg) challenges. Sera were collected after LPS or EORP challenge for assessment of IL-1 and IL-1Ra expression.

Materials

LPS, FITC-LPS (from *Escherichia coli* 0111:B4), Histopaque®-1077, anti-MAP kinase, activated (diphosphorylated ERK) antibody, anti-JNK kinase, activated (diphosphorylated JNK) antibody, anti-p38 MAP kinase, activated (diphosphorylated p38) antibody, and anti-actin antibody were purchased from Sigma Co. (St. Louis, Mo.). Anti-rabbit IgG-HRP, anti-mouse IgG-HRP, and anti-IL-1 antibody were obtained from Santa Cruz Biotechnology (Santa Cruz, Calif.); anti-mouse TLR4 blocking antibody and PE-conjugated anti-mouse TLR4 antibody were obtained from IMGENEX Corporation (Carlsbad, Calif.); PE-conjugated anti-mouse CD14 antibody was obtained from BD Biosciences (Mountain View, Calif.); anti-mouse macrophage scavenger receptor (MSR) antibody (2F8) and FITC-conjugated MSR antibody were obtained from Serotec, Inc. (Oxford, UK). Mouse IL-1 Enzyme-Linked Immunosorbent Assay Kit was purchased from R&D Systems, Inc. (Minneapolis, Minn.). Human IL-1 and TNF Enzyme-Linked Immunosorbent Assay (ELISA) Kit were purchased from BioSource International, Inc (Camarillo, Calif.). Primers for RT-PCR of IL-1 and glyceraldehydes phosphate dehydrogenase (GAPDH) were synthesized from MDBio. Inc. (Taipei, Taiwan). The LysoTracker™ Red DND-99 and BODIPY TR $C_5$-ceramide were purchased from Molecular Probes, Inc. (Eugene, Oreg.).

Preparation of extract of Reishi polysaccharides (EORP), RNA isolation, RT and PCR amplification for detecting the expression of IL-1, Western Blotting Analysis, Enzyme-Linked Immunosorbent Assay (ELISA) for measurement of IL-1 and ICE activity assay.

Flow Cytometry Analysis

For cell surface expression experiments of TLR4, CD14, and MSR, J774A.1 cells were incubated with medium (control), EORP (25 g/mL), LPS (1 µg/mL), fucoidan (25 µg/mL), F1 fraction of Reishi (25 µg/mL) or F2 fraction of Reishi (25 µg/mL) for 24 h. Cells were fixed and cell surface expression of TLR4, CD14 or MSR were measured by staining cells for 30 min with PE-conjugated anti-TLR4 antibody, PE-conjugated anti-CD14 antibody or FITC-conjugated MSR antibody on ice, respectively. After washing, cells were subjected to flow cytometric analysis on FACSCalibur using CellQuest software of Becton Dickinson Inc. (San Jose, Calif.). Experiments for binding of LPS to cell surface, J774A.1 cells were incubated with medium, EORP (25 µg/mL) or LPS (1 µg/mL) for 24 h. After fixation, cells were incubated with FITC-LPS for 30 min at 4° C. After washing, cells were subjected to flow cytometry analysis. For LPS uptake experiments, J774A.1 cells were incubated with medium, EORP (25 µg/mL) or LPS (1 µg/mL) for 24 h. After washing, cells were incubated with FITC-LPS for 1 h at 37° C. After incubation, cells were washed twice with PBS and further treated with proteinase K (250 µg/mL) for 30 min at room temperature to remove cell surface proteins/receptors and surface-bound LPS [92]. The remaining LPS were considered to be intracellular and FITC-LPS in J774A.1 cells was measured by flow cytometric analysis.

Confocal Microscope Analysis

For LPS cell surface binding experiments, J774A.1 cells were incubated with medium or EORP (25 µg/mL) for 24 h. Cells were fixed and incubated with TLR4 blocking antibody (10 µg/mL), CD14-blocking antibody (10 µg/mL), or control antibody (10 µg/mL) for 30 min, followed by incubation of FITC-LPS for 30 min at 4° C. For LPS uptake experiments, cells were incubated with medium or EORP (25 µg/mL) for 24 h. After washing, cells were incubated with TLR4 blocking antibody (10 µg/mL), CD14-blocking antibody (10 µg/mL), control antibody (10 µg/mL), cytochalasin D (10 µM) or colchicines (30 µM) for 30 min, followed by incubation of FITC-LPS for 1 h at 37° C. For TLR4 and CD14 expression, cells were incubated with EORP (25 µg/mL) for 24 h, followed by staining with PE-conjugated anti-TLR4 antibody or PE-conjugated anti-CD14 antibody for 2 h at room temperature. For LPS/lysosomes co-localization experiments, cells were incubated with EORP (25 µg/mL) for 24 h. After washing, cells were incubated with FITC-LPS (1 µg/mL) and LysoTracker™ Red DND-99 (100 nM) at 37° C. for 0 to 120 min. For LPS/Golgi co-localization experiments, cells were incubated with EORP (25 µg/mL) for 24 h. After washing, cells were incubated with BODIPY TR $C_5$-ceramide (5 µM) at 4° C. for 30 min, followed by incubated with FITC-LPS (1 µg/mL) at 37° C. for additional 0 to 120 min. After washing, cells were visualized using a Leica TLS SP2 confocal microscope (Leica Lasertechnik, Heidelberg, Germany).

Statistical Analysis

Statistical differences between the experimental groups were examined by analysis of variance, and statistical significance was determined at $p<0.05$. The experiments were conducted three times or as indicated, all data are expressed as mean±S.E.

Many modifications and variations are possible in the light of the above teachings. The foregoing is a description of the preferred embodiments of the disclosure and has been presented for the purpose of illustration and description. It is not intended to be exhaustive and so limit the disclosure to the precise form disclosed.

The disclosures of each and every publication and reference cited in the present description, which include any accompanying papers, which form part thereof, are hereby incorporated by reference in their entirety, in the present disclosure. The citation of each publication and reference is not to be taken as an admission that the disclosure of that publication and reference forms part of the body of prior art in any country.

REFERENCES

[1] Aderem A. and Ulevitch R. J., *Nature* 2000 406, pp. 782-787.

[2] Akira, S., K. Takeda, and T. Kaisho in Nat. Immunol. 2001 2:675.

[3] Ando I., Tsukumo Y., Wakabayashi T., Akashi S., Miyake K., Kataoka T. and Nagai K., *Int. Immunopharmacol.* 2002 2, pp. 1155-1162.

[4] Bao, X. F., X. S. Wang, Q. Dong, J. N. Fang, and X. Y. Li. In Phytochemistry 2002 59:175.

[5] Bowden R., Tate S. M., Soto S. and Specter S. *Int. J. Immunopharmacol* 1999 21, p. 815.

[6] Brown, G. D., P. R. Taylor, D. M. Reid, J. A. Willment, D. L. Williams, L. Martinez-Pomares, S. Y. C. Wong, and S. Gordon. In J. Exp. Med. 2002 196:407.

[7] Calame, K. L., K. I. Lin, and C. Tunyaplin, *Regulatory mechanisms that determine the development and function of plasma cells*. Annu Rev Immunol, 2003. 21: p. 205-30.

[8] Chen H., Tsai Y., Lin S., Lin C., Khoo K., Lin C. and Wong C., Studies on the immuno-modulating and anti-tumor activities of *Ganoderma lucidum* (Reishi) polysaccharides, Bioorganic & Medicinal Chemistry, 2004 vol. 12, iss. 21, pages 5595-5601.

[9] Chien C., Chen J., Chang W., Tien M. Tsao C. Chang Y. Chang H., Hsieh J., Wong C. and Chen S., Bioorganic Medicinal Chemistry 2004, 12, pp. 5603-5609

[10] Carter R. H., Wang Y. and Brooks S., *Immunol. Res.* 2002 26, p. 45.

[11] Colucci F., Caligiuri M. A. and Di Santo J. P., *Nat. Rev. Immunol.* 2003 3, p. 413.

[12] Cooper M. A., Fehniger T. A. and Caligiuri M. A., *Trends Immunol.* 2001 22, p. 633.

[13] Dobrovolskaia M. A. and Vogel S. N., *Microbes. Infect.* 2002 4, p. 903.

[14] Foley R., Tozer R. and Wan Y., *Transfus. Med. Rev.* 2001 15, p. 292.

[15] Gritzapis A. D., Dimitroulopoulos D., Paraskevas E., Baxevanis C. N. and Papamichail M., *Cancer Immunol. Immunother.* 2002 51, p. 440.

[16] Halhoul M. N. and Kleinberg I. *Anal. Biochem.* 1972 (50), p. 337.

[17] Hatada E. N., Krappmann D. and Scheidereit C., *Curr. Opin. Immunol.* 2000 12, pp. 52-58.

[18] Hoshino, K., O. Takeuchi, T. Kawai, H. Sanjo, T. Ogawa, Y. Takeda, K. Takeda, and S. Akira. J. Immunol. 1991 162:3749.

[19] Hsu, H. Y. et al., *J. Immunol*. in press.

[20] Hsu, H. Y., and M. H. Wen. 2002 in J. Biol. Chem. 2002 277:22131.

[21] Hsu, H. Y., and Y. C. Twu. in J. Biol. Chem. 2000 275:41035.

[22] Hsu, H. Y., S. L. Chiu, M. H. Wen, K. Y. Chen, and K. F. Hua. in J. Biol. Chem. 2001 276:28719.

[23] Imler J. L. and Hoffmann J. A., *Trends Cell Biol.* 2001 11, pp. 304-311.

[24] Jermyn M. A. *Anal. Biochem.* 1975 (68), p. 332.

[25] Joshi S. S., Babushkina-Patz N. N., Verbik D. J., Gross T. G., Tarantolo S. R., Kuszynski C. A., Pirruccello S. J., Bishop M. R. and Kessinger A., *Int. J. Oncol.* 1998 13, p. 791.

[26] Klein J. B., Rane M. J., Scherzer J. A., Coxon P. Y., Kettritz R., Mathiesen J. M., Buridi A. and McLeish K. R, *J. Immunol.* 2000 164, pp. 4286-4291.

[27] Lee, S. S., Y. H. Wei, C. F. Chen, S. Y. Wang, and K. Y. Chen. In J. Chin. Med. 1995 6:1.

[28] Lehner, M. D., S. Morath, K. S. Michelsen, R. R. Schumann, and T. Hartung. J. Immunol. 2001 166:5161.

[29] Lien, E. J. in Drug Research, Birkhauser, Basel, 1990 34, p. 395.

[30] Mak T. W. and Yeh W.-C., in *Nature* 2002 418, pp. 835-836.

[31] Mambula, S. S., Sau K., Henneke P., Golenbock D. T, and Levitz S. M. in J. Biol. Chem. 2002 277:39320.

[32] Manser, E., C. Chong, Z. S. Zhao, T. Leung, G. Michael, C. Hall, and L. Lim. In J. Biol. Chem. 1995 270:25070.

[33] Miyazaki T. and Nishijime M. *Carbohydr. Res.* 1982 109, p. 290.

[34] Miyazaki, T., and M. Nishijima. in Chem. Pharm. Bull. 1981 29:3611.

[35] Morimoto C. and Schlossman S. F., *Immunol. Rev.* 1998 161, p. 55.

[36] Mosmanni T. *J. Immunol. Methods* 1983 (65), p. 55.

[37] Muller A., Rice P. J., Ensley H. E., Coogan P. S., Kalbfleisch J. H., Kelley J. L., Love E. J., Portera C. A., Ha T., Browder I. W. and Williams D. L., *J. Immunol.* 1996 156, pp. 3418-3425.

[38] Muller, P. J. Rice, H. E. Ensley, P. S. Coogan, J. H. Kalbfleisch, J. L. Kelley, E. J. Love, C. A. Portera, T. Ha, I. W. Browder and D. L. Williams *J. Immunol.* 1996 156, p. 3418.

[39] Muroi M. and Tanamoto K., *Infect. Immun.* 2002 70, pp. 6043-6047.

[40] Murphy E., Hieny S., Sher A. and O'Garra A. *J. Immunol. Methods* 162 (1993), p. 211.

[41] Muzio, M., and A. Mantovani. Toll-like receptors. Microbes Infect. 2000 2:251.
[42] Penninger J. M., Irie-Sasaki J., Sasaki T. and Oliveira-dos-Santos A. J., *Nat. Immunol.* 2001 2 p. 389.
[43] Poltorak, A., X. He, I. Smirnova, M. Y. Liu, C. V. Huffel, X. Du, D. Birdwell, E. Alejos, M. Silva, C. Galanos, et al. Science 1998 282:2085.
[44] Qureshi, S. T., L. Lariviere, G. Leveque, S. Clermont, K. J. Moore, P. Gros, and D. Malo. J. Exp. Med. 1999 189:615.
[45] Roehm N. W., Rodgers G. H., Hatfield S. M. and Glasebrook A. L., *J. Immunol. Methods* 1991 142, p. 257.
[46] Sanchez J.-C., Chiappe D., Converset V., Hoogland C., Binz P.-A., Paesano S., Appel R. D., Wang S., Sennitt M., Norlan A., Cawthorne M. A. and Hochstrasser D. F. *Proteomics* 1 (2001), p. 136.
[47] Schantz S. P., Brown B. W., Lira E., Taylor D. L. and Beddingfield N., *Cancer. Immunol. Immunother.* 1987 25, p. 141.
[48] Scudiero D. A., Shoemaker R. H., Paull K. D., Monks A., Tierney S., Nofziger T. H., Currens M. J., Seniff D. and Boyd M. R., *Cancer. Res.* 1988 48, p. 4827.
[49] Shiao, M. S., K. R. Lee, L. J. Lin, and C. T. Wang. in Food Phytochemicals for Cancer Prevention II: Teas, Spices, and Herbs. C. T. Ho, T. Osawa, M. T. Huang, and R. T. Rosen, eds. American Chemical Society, Washington D.C., 1994 p. 342.
[50] Shimazu, R., S. Akashi, H. Ogata, Y. Nagai, K. Fukudome, K. Miyake, and M. Kimoto. in J. Exp. Med. 1999 189:1777.
[51] Smith J. A. and Bluestone J. A., *Curr. Opin. Immunol.* 1997 9, p. 648.
[52] Somani B. L., Khanade J. and Sinha R. *Anal. Biochem.* 167 (1987), p. 327.
[53] Spachman D. H., Moore S. and Stein W. H. *Anal. Chem.* 30 (1958), p. 1190 For a recent example, please see: Lo, C.-H.; Chiou, S.-H. *J. Chromatogr.* 1990, 530, 129
[54] Stone Y., Okuda R. and Wada N., *Agr. Biol. Chem.* 1985 49, pp. 2641-2653.
[55] Stone, Y., R. Okuda, N. Wada, E. Kishida, and A. Misaki. in Agric. Biol. Chem. 1985 49:2641.
[56] Usui T., Iwasaki Y. and Mizuno T. in *Carbohydr. Res.* 115 (1983), p. 273.
[57] Van Strijp J. A. G., Russel D. G., Tuomanen E., Brown E. J. and Wright S. D., *J. Immunol.* 1993 151, pp. 3324-3336.
[58] Vetvicka V., Thornton B. P. and Ross G. D., *J. Clin. Invest.* 1996 98, pp. 50-61.
[59] Wang S.-Y., Hsu M.-L. and Hsu H., *Int. J. Cancer* 1997 70, pp. 699-705.
[60] Wang S. Y., Hsu M. L., Hsu H. C., Tzeng C. H., Lee S. S., Shiao M. S. and Ho C. K., *Int. J. Cancer* 1997 70, p. 699.
[61] Wang Y. Y., Khoo K. H., Chen S. T., Lin C. C., Wong C. H. and Lin C. H., *Bioorg. Med. Chem.* 2002 10, p. 1057.
[62] Wang, G., J. Zhang, T. Mizuno, C. Zhuang, H. Ito, H. Mayuzumi, H. Okamoto, and J. Li. in Biosci. Biotechnol. Biochem. 1993 57:894.
[63] Wang, S. Y., M. L. Hsu, H. C. Hsu, C. H. Tzeng, S. S. Lee, M. S. Shiao, and C. K. Ho. in Int. J. Cancer 1997 70:699.
[64] Warren H. S., Christiansen F. T. and Witt C. S., *Br. J. Haematol.* 2003 121, p. 793.
[65] Won S. J., Lin M. T. and Wu W. L., *Jpn. J. Pharmacol.* 1992 59, p. 171.
[66] Zhang J., Wang G., Li H., Zhuang C., Mizuno T., Ito H., Mayuzumi H., Okamoto H. and Li J., *Biosci. Biotechnol. Biochem.* 1994 58, p. 1202.
[67] Zhang L., Zhang M., Zhou Q., Chen J. and Zeng F., *Biosci. Biotechnol. Biochem.* 2000 64, p. 2172.
[68] Bioorg Med Chem, 2004, Vol. 12, 5595
[69] Wang, Y. Y., K. H. Khoo, S. T. Chen, C. C. Lin, C. H. Wong, C. H. Lin. 2002. Studies on the Immuno-Modulating and Antitumor Activities of *Ganoderma lucidum* (Reishi) Polysaccharides: Functional and Proteomic Analyses of a Fucose-Containing Glycoprotein Fraction Responsible for the Activities. *Bioorg. Med. Chem.* 10(4): 1057-1062.
[70] Hsu, H. Y., K. F. Hua, C. C. Lin, C. H. Lin, J. Hsu, and C. H. Wong. 2004. Extract of Reishi Polysaccharides Induces Cytokine Expression via Toll-like Receptor 4-modulated Protein Kinase Signaling Pathways. *J. Immunol.* 173(10): 5989-5999.
[71] Iwasaki, A. and R. Medzhitov. 2004. Toll-like receptor control of the adaptive immune responses. *Nat. Immunol.* 5(10): 987-995.
[72] Gordon, S. 2002. Pattern recognition receptors: doubling up for the innate immune response. *Cell* 111(7): 927-930.
[73] Raetz, C. R. and C. Whitfield. 2002. Lipopolysaccharide Endotoxins. *Annu. Rev. Biochem.* 71: 635-700.
[74] Goyert, S. M., E. Ferrero, W. J. Rettig, A. K. Yenamandra, F. Obata, and M. M. Le Beau. 1988. The CD14 monocyte differentiation antigen maps to a region encoding growth factors and receptors. *Science* 239(4839): 497-500.
[75] Poltorak, A., X. He, I. Smirnova, M. Y. Liu, C. Van Huffel, X. Du, D. Birdwell, E. Alejos, M. Silva, C. Galanos, M. Freudenberg, P. Ricciardi-Castagnoli, B. Layton, and B. Beutler. 1998. Defective LPS signaling in C3H/HeJ and C57BL/10ScCr mice: mutations in Tlr4 gene. *Science* 282(5396): 2085-2088.
[76] Stuart, L. M., and R. A. Ezekowitz. 2005. Phagocytosis: elegant complexity. *Immunity* 22(5): 539-550.
[77] Munford, R. S., and C. L. Hall. 1986. Detoxification of bacterial lipopolysaccharides (endotoxins) by a human neutrophil enzyme. *Science* 234: 203-205.
[78] Dunzendorfer, S., H. K. Lee, K. Soldau, and P. S. Tobias. 2004. TLR4 Is the Signaling but Not the Lipopolysaccharide Uptake Receptor. *J. Immunol.* 173(2): 1166-1170.
[79] Latz, E., A. Visintin, E. Lien, K. A. Fitzgerald, B. G. Monks, E. A. Kurt-Jones, D. T. Golenbock, and T. Espevik. 2002. Lipopolysaccharide rapidly traffics to and from the Golgi apparatus with the Toll-like receptor 4-MD-2-CD14 complex in a process that is distinct from the initiation of signal transduction. *J. Biol. Chem.* 277(49): 47834-47843.
[80] Hampton, R. Y., D. T. Golenbock, M. Penman, M. Krieger, and C. R. Raetz. 1991. Recognition and plasma clearance of endotoxin by scavenger receptors. *Nature* 352: 342-344.
[81] Cowan, D. B., S. Noria, C. Stamm, L. M. Garcia, D. N. Poutias, P. J. del Nido, and F. X. McGowan, Jr. 2001. Lipopolysaccharide Internalization Activates Endotoxin-Dependent Signal Transduction in Cardiomyocytes. *Circ Res.* 88(5): 491-498.
[82] Poussin, C., M. Foti, J. L. Carpentier, and J. Pugin. 1998. CD14-dependent Endotoxin Internalization via a Macropinocytic Pathway. *J. Biol. Chem.* 273(32): 20285-20291.
[83] Hsu, M. J., S. S. Lee, S. T. Lee, and W. W. Lin. 2003. Signaling mechanisms of enhanced neutrophil phagocytosis and chemotaxis by the polysaccharide purified from *Ganoderma lucidum*. *Br. J. Pharmacol.* 139(2): 289-298.
[84] Dinarello, C. A. 1996. Biologic basis for interleukin-1 in disease. *Blood* 87: 2095-2147.
[85] Cerretti, D. P., C. J. Kozlosky, B. Mosley, N. Nelson, K. Van Ness, T. A. Greenstreet, C. J. March, S. R. Kronheim, T. Druck, L. A. Canniz, et al. 1992. Molecular cloning of the interleukin-1 beta converting enzyme. *Science* 256(5053): 97-100.

[86] Loppnow, H., K. Werdan, G. Reuter, H. D. Flad. 1998. The interleukin-1 and interleukin-1 converting enzyme families in the cardiovascular system. *Eur. Cytokine Network* 9: 675-680.

[87] Joshi, V. D., D. V. Kalvakolanu, J. R. Hebel, J. D. Hasday, and A. S. Cross. 2002. Role of caspase 1 in murine antibacterial host defenses and lethal endotoxemia. *Infect Immun.* 70(12): 6896-6903.

[88] Waage, A. and T. Espevik. 1988. Interleukin 1 potentiates the lethal effect of tumor necrosis factor alpha/cachectin in mice. *J. Exp. Med.* 167: 1987-1992.

[89] Kay, J. and L. Calabrese. 2004. The role of interleukin-1 in the pathogenesis of rheumatoid arthritis. Rheumatology 43: Suppl 3: iii2-iii9.

[90] Hannum, C. H., C. J. Wilcox, W. P. Arend, F. G. Joslin, Dripps, D. J., P. L. Heimdal, L. G. Armes, A. Sommer, S. P. Eisenberg, and R. C. Thompson. 1990. Interleukin-1 receptor antagonist activity of a human interleukin-1 inhibitor. *Nature* 343: 336-340.

[91] Hirsch, E., V. M. Irikura, S. M. Paul, and D. Hirsh. 1996. Functions of interleukin-1 receptor antagonist in gene knockout and overproducing mice. *Proc. Natl. Acad. Sci. USA* 93: 11008-11013.

[92] Kitchens, R. L., and R. S. Munford. 1998. CD14-dependent internalization of bacterial lipopolysaccharide (LPS) is strongly influenced by LPS aggregation but not by cellular responses to LPS. *J. Immunol.* 160(4): 1920-1928.

[93] Hsu, H. Y. and M. W. Wen. 2002. Lipopolysaccharide-mediated reactive oxygen species and signal transduction in the regulation of interleukin-1 gene expression. *J. Biol. Chem.* 277(25): 22131-22139.

[94] Hsu, H. Y., S. L. Chiu, M. H. Wen, K. Y. Chen, K. F. Hua. 2001. Ligands of macrophage scavenger receptor induce cytokine expression via differential modulation of protein kinase signaling pathways. *J. Biol. Chem.* 276(31):28719-28730.

[95] Nomura, F., S. Akashi, Y. Sakao, S. Sato, T. Kawai, M. Matsumoto, K. Nakanishi, M. Kimoto, K. Miyake, K. Takeda, and S. Akira. 2000. Cutting edge: endotoxin tolerance in mouse peritoneal macrophages correlates with down-regulation of surface toll-like receptor 4 expression. *J. Immunol.* 164(7): 3476-3479.

[96] Via, L. E., R. A. Fratti, M. McFalone, E. Pagan-Ramos, D. Deretic, and V. Deretic. 1998. Effects of cytokines on mycobacterial phagosome maturation. *J. Cell Sci.* 111: 897-905.

[97] Thieblemont, N. and S. D. Wright. 1997. Mice genetically hyporesponsive to lipopolysaccharide (LPS) exhibit a defect in endocytic uptake of LPS and ceramide. *J. Exp. Med.* 185(12): 2095-2100.

[98] Lipsky, N. G. and R. E. Pagano. 1985. A vital stain for the Golgi apparatus. *Science.* 228(4700): 745-747.

[99] Kriegsmann, J., S. Gay, and R. Brauer. 1993. Endocytosis of lipopolysaccharide in mouse macrophages. *Cell Mol. Biol.* 39(7): 791-800.

[100] Cooper, J. A. 1987. Effects of cytochalasin and phalloidin on actin. *J. Cell Biol.* 105(4): 1473-1478.

[101] Isowa, N., A. M. Xavier, E. Dziak, M. Opas, D. I. McRitchie, A. S. Slutsky, S. H. Keshavjee, and M. Lui. 1999. LPS-induced depolymerization of cytoskeleton and its role in TNFa production by rat pneumocytes. *Am J Physiol.* 277: L606-615.

[102] Fearon, D. T. and R. M. Locksley. 1996. The instructive role of innate immunity in the acquired immune response. *Science* 272(5258): 50-53.

[103] Tobias, P. S., K. Soldau, L. Kline, J. D. Lee, K. Kato, T. P. Martin, and R. J. Ulevitch. 1993. Cross-linking of lipopolysaccharide (LPS) to CD14 on THP-1 cells mediated by LPS-binding protein. *J. Immunol.* 150(7): 3011-3021.

[104] Zigmond, S. H. 1996. Signal transduction and actin filament organization. *Curr. Opin. Cell Biol.* 1996 8(1): 66-73.

[105] Bocker, U., O. I. Sirenko, J. S. Morris, R. B. Sartor, M. V. Singer, J. S. Haskill, and J. M. Watson. 2001. Expression and localization of IL-1beta mRNA is interrelated with cytoskeletal rearrangement in monocytes stimulated by adherence: a light microscopy in situ hybridization study. *Immunol. Cell Biol.* 79(5): 444-453.

[106] Leesun, K., B. A. Butcher, and E. Y. Denkers. 2004. *Toxoplasma gondii* Interferes with Lipopolysaccharide-Induced Mitogen-Activated Protein Kinase Activation by Mechanisms Distinct from Endotoxin Tolerance. *J. Immunol.* 172(5): 3003-3010.

[107] Karahashi, H. and F. Amano. 2003. Endotoxin-Tolerance to the Cytotoxicity toward a Macrophage-Like Cell Line, J774.1, Induced by Lipopolysaccharide and Cycloheximide: Role of p38 MAPK in Induction of the Cytotoxicity. *Biol. Pharm. Bull.* 26(9): 1249-1259.

[108] Dobrovolskaia, M. A., A. E. Medvedev, K. E. Thomas, N. Cuesta, V. Toshchakov, T. Ren, M. J. Cody, S. M. Michalek, N. R. Rice, and S. N. Vogel. 2003. Induction of In Vitro Reprogramming by Toll-Like Receptor (TLR) 2 and TLR4 Agonists in Murine Macrophages: Effects of TLR "Homotolerance" Versus "Heterotolerance" on NF-KB Signaling Pathway Components. *J. Immunol.* 170(1): 508-519.

[109] Kobayashi, K., L. D. Hernandez, J. E. Galan, C. A. Jr. Janeway, R. Medzhitov and R. A. Flavell. 2002. IRAK-M is a negative regulator of Toll-like receptor signaling. *Cell* 110(2): 191-202.

[110] Arend W. P., M. Malyak, C. J. Guthridge, and C. Gabay. 1998. Interleukin-1 receptor antagonist: Role in Biology. *Annu. Rev. Immunol.* 16: 27-55.

What is claimed is:

1. A method comprising administering an effective amount of terminal fucose-containing glycoprotein fraction from *Ganoderma lucidum* to a lipopolysaccharide (LPS)-stimulated macrophage prior to or during LPS Stimulation to increase the secretion of IL-1 by the macrophage, wherein the terminal fucose-containing fraction is a fraction of *Ganoderma lucidum* extract prepared by dissolving raw *Ganoderma lucidum* in a solvent to form a solution, fractioning the solution according to molecular weight, and designating as the terminal fucose-containing glycoprotein fraction the fraction having a light absorbance of about 1.8 at O.D. 625 nm.

2. A method comprising administering an effective amount of a terminal fucose-containing glycoprotein fraction from *Ganoderma lucidum* to a mammal prior to or during contact of the mammal with a lipopolysacoharide to increase the serum level of IL-1 that is produced in response to introduction of the lipopolysaccharide into the mammal, wherein the terminal fucose-containing fraction is a fraction of *Ganoderma lucidum* extract prepared by dissolving raw *Ganoderma lucidum* in a solvent to form a solution, fractioning the solution according to molecular weight, and designating as the terminal fucose-containing glycoprotein fraction the fraction having a light absorbance of about 1.8 at O.D. 625 nm.

3. A method comprising administering an effective amount of a terminal fucose-containing glycoprotein fraction from *Ganoderma lucidum* to a mammal to increase the serum level of IL-1 receptor antagonist in the mammal, wherein the terminal fucose-containing fraction is a fraction of *Ganoderma lucidum* extract prepared by dissolving raw *Ganoderma luci-*

*dum* in a solvent to form a solution, fractioning the solution according to molecular weight, and designating as the terminal fucose-containing glycoprotein fraction the fraction having a light absorbance of about 1.8 at O.D. 625 nm.

4. A method comprising administering an effective amount of a terminal fucose containing glycoprotein fraction from *Ganoderma lucidum* to a monocyte to increase the secretion of IL-1 by the monocyte, wherein the terminal fucose-containing fraction is a fraction of *Ganoderma lucidum* extract prepared by dissolving raw *Ganoderma lucidum* in a solvent to form a solution, fractioning the solution according to molecular weight, and designating as the terminal fucose-containing glycoprotein fraction the fraction having a light absorbance of about 1.8 at O.D. 625 nm.

5. A method comprising administering an effective amount of a terminal fucose-containing glycoprotein fraction from *Ganoderma lucidum* to a monocyte to increase the secretion of IL-1 receptor antagonist by the monocyte, wherein the terminal fucose-containing fraction is a fraction of *Ganoderma lucidum* extract prepared by dissolving raw *Ganoderma lucidum* in a solvent to form a solution, fractioning the solution according to molecular weight, and designating as the terminal fucose-containing glycoprotein fraction the fraction having a light absorbance of about 1.8 at O.D. 625 nm.

6. A method comprising administering an effective amount of a terminal fucose-containing glycoprotein fraction from *Ganoderma lucidum* to a macrophage to increase the secretion of IL-1 receptor antagonist by the macrophage, wherein the terminal fucose-containing fraction is a fraction of *Ganoderma lucidum* extract prepared by dissolving raw *Ganoderma lucidum* in a solvent to form a solution, fractioning the solution according to molecular weight, and designating as the terminal fucose-containing glycoprotein fraction the fraction having a light absorbance of about 1.8 at O.D. 625 nm.

* * * * *